United States Patent [19]

Schoendorfer

[11] Patent Number: 5,465,713
[45] Date of Patent: Nov. 14, 1995

[54] ENERGY-ASSISTED TRANSDERMAL COLLECTION PATCH FOR ACCELERATED ANALYTE COLLECTION AND METHOD OF USE

[75] Inventor: Donald W. Schoendorfer, Santa Ana, Calif.

[73] Assignee: Sudor Partners, Santa Ana, Calif.

[21] Appl. No.: 94,787

[22] Filed: Jul. 20, 1993

Related U.S. Application Data

[63] Continuation-in-part of Ser. No. 39,631, Mar. 30, 1993, which is a continuation-in-part of Ser. No. 989,204, Dec. 11, 1992, which is a continuation-in-part of Ser. No. 569,007, Aug. 15, 1990, Pat. No. 5,203,327, which is a continuation-in-part of Ser. No. 241,707, Sep. 8, 1988, Pat. No. 4,957,108.

[51] Int. Cl.$^6$ ......................................................... A61B 5/00
[52] U.S. Cl. ........................... 128/632; 128/636; 128/760; 128/771
[58] Field of Search ..................................... 128/632, 636, 128/637, 760, 771; 604/312

[56] References Cited

U.S. PATENT DOCUMENTS

| | | |
|---|---|---|
| 32,026 | 11/1985 | Yamashita . |
| 3,552,929 | 1/1971 | Fields et al. . |
| 3,976,049 | 8/1976 | Yamashita . |
| 4,190,060 | 2/1980 | Greenleaf et al. . |
| 4,266,556 | 5/1981 | Barlow et al. ........................... 128/760 |
| 4,287,153 | 9/1981 | Townsend . |
| 4,329,999 | 5/1982 | Phillips . |
| 4,341,207 | 7/1982 | Steer et al. . |
| 4,360,015 | 11/1982 | Mayer . |
| 4,401,122 | 8/1983 | Clark, Jr. . |
| 4,444,193 | 4/1984 | Fogt et al. . |
| 4,542,751 | 9/1985 | Webster et al. . |
| 4,595,011 | 6/1986 | Phillips . |
| 4,631,174 | 12/1986 | Kondo . |
| 4,667,665 | 5/1987 | Blanco et al. . |
| 4,706,676 | 11/1987 | Peck . |
| 4,732,153 | 3/1988 | Phillips . |
| 4,756,314 | 7/1988 | Eckenhoff et al. . |
| 4,775,361 | 10/1988 | Jacques et al. . |
| 4,821,733 | 4/1989 | Peck . |
| 4,909,256 | 3/1990 | Peck . |
| 4,957,108 | 9/1990 | Schoendorfer et al. . |
| 4,960,467 | 10/1990 | Peck . |
| 5,036,861 | 8/1991 | Sembrowich et al. . |
| 5,076,273 | 12/1991 | Schoendorfer et al. ................. 128/632 |
| 5,094,248 | 3/1992 | Kawam . |
| 5,131,390 | 7/1992 | Sakaguchi et al. ..................... 128/760 |

FOREIGN PATENT DOCUMENTS

| | | |
|---|---|---|
| 0099748 | 2/1987 | European Pat. Off. . |
| 0217430 | 4/1987 | European Pat. Off. . |
| 0135646 | 6/1986 | Japan ..................................... 128/760 |
| 2157955 | 11/1985 | United Kingdom . |
| WO8904630 | 6/1989 | WIPO . |

OTHER PUBLICATIONS

Phillips et al, "Long–Ferm Sweat Collection . . . ", the J of Investigative Dermatology, 68:221–224, 1977.

Jackson, et al., Clinical Chemistry, vol. 30, No. 7, 1984, pp. 1157–1162, "Two–site monoclonal antibody assays for human heart–and–brain–type creatine kinase".

Howard, Michael J., et al., editors, *Films, Sheets, and Laminates, a desktop data bank*©, The International Plastics Selector, Inc., San Diego, Calif. pp. xli, B–269, B–296, B–358, B–524, B–893 (no author listed).

Abuscreen© Radioimmunoassay for Cocaine Metabolite, Product Insert, Roche Diagnostic Systems, Inc., Nov., 1987, Nutley, N.J. (numbers of relevant pages unknown). No (List continued on next page.)

*Primary Examiner*—Lee S. Cohen
*Attorney, Agent, or Firm*—Knobbe Martens Olson & Bear

[57] ABSTRACT

A dermal patch including a means for generating heat on the surface of the skin of a subject wearing the patch. The temperature of the surface of the skin under the patch is raised to about 115° F., and perspiration is collected in the patch over the course of about an hour. The patch is then analyzed to determine the presence of an analyte in the patch.

20 Claims, 10 Drawing Sheets

OTHER PUBLICATIONS author cited.

Coat–A–Count© Cocaine Metabolite, Product Insert, DPC Diagnostic Products Corporation, May 11, 1989, Los Angeles, pp. 1–13. No author cited.

Weast, Robert C., ed., "Physical Constants of Organic Compounds," Handbook of Chemistry and Physics, 47th ed., 1966, p. C–247 (author unknown).

Aly, Raza, Ph.D., et al., "Effect of Prolonged Occlusion on the Microbial Fluora, pH, Carbon Dioxide and Transepidermal Water Lost on Human Skin," *The Journal of Investigative Dermatology*, vol. 71, No. 6, 71:378–381 (1978).

Labaune, Jean–Pierre, *Handbook of Pharmacokinetics: Toxicity Assessment of Chemicals*, pp. 16–25 (1989).

Ashburn, Michael, M.D., et al., "Iontophoretic Delivery of Morphine for Postoperative Analgesia," *Journal of Pain and Symptom Management*, vol. 7, No. 1, pp. 27 et seq. (Jan. 1992).

Peck, Carl C., et al., "Continuous Transepidermal Drug Collection: Basis for Use in Assessing Drug Intake and Pharmacokinetics," *Journal of Pharmacokinetics and Biopharmacology*, vol. 9, No. 1, pp. 41–58 (1981).

Odland, George F., "Structure of the Skin," *Physiology, Biochemistry and Molecular Biology of the Skin*, Lowell A. Goldsmith, M. D., editor, 2nd ed., pp. 3–62 (1991).

Shaw, Jane E., et al., "Percutaneous Absorption," *Physiology, Biochemistry and Molecular Biology of the Skin*, Lowell A. Goldsmith, M.D., editor, 2nd ed., pp. 1447–1479 (1991).

Sato, Kenzo, "Biology of Eccrine Sweat Glands," *Physiology, Biochemistry and Molecular Biology of the Skin*, Lowell A. Goldsmith, M.D., editor, 2nd ed., pp. 741–762 (1991).

Gibson, Lewis E., M. D., et al., "A Test for Concentration of Electrolytes in sweat in Cystic Fibrosis of the Pancreas Utilizing Pilocarpine by Iontophoresis", *Pediatrics*, pp. 545–549 (Mar. 1959).

Brebner, D. F., et al., "The Time Course of the Decline in Sweating Produced by Wetting the Skin", *J. Physiol.*, vol. 175, pp. 295–302 (May 28 1964).

Feldmann, Robert J., M.D. et al., "Penetration of $^{14}$C Hydrocortisone Through Normal Skin", *Arch. Dermat.*, vol. 91, pp. 661–666 (Jun. 1965).

Darwin, et al., "Identification of Drug Analytes Excreted in Sweat after Cocaine and Heroin Administration", Abstract presented at 1993 Joint Meeting: Society of Forensic Toxicologists & California Association of Toxicologists, Aug.–Sep. 1993 (one page).

Hillsgrove, et al., "Kinetic Studies of Cocaine Excretion in Sweat", Abstract presented at 1993 Joint Meeting: Society of Forensic Toxicologists & California Association of Toxicologists, Aug.–Sep. 1993 (one page).

Burns, et al., "Use of a Skin Patch to Monitor Cocaine Abuse", Abstract presented at 1993 Joint Meeting: Society of Forensic Toxicologists & California Association of Toxicologists, Aug.–Sep. 1993 (one page).

Hillsgrove, et al., "Monitoring Cocaine Abuse with a Sweat Patch", Abstract presented at 1993 Joint Meeting: Society of Forensic Toxicologists & California Association of Toxicologists, Aug.–Sep. 1993 (one page).

Fay, et al. "Sweat Eluate Analysis for Cocaine, Benzoylecgonine, and Ecgonine Methyl Ester by STC Diagnostics Cocaine Micro–Plate EIA and GC/MS", Abstract presented at 1994 Annual Meeting of the American Academy of Forensic Sciences, Inc., Dec. 1993 (one page).

Kahn, Jason, "Sweat Collection Patch Could Aid in Monitoring Illicit Drugs", *Clinical Chemistry News*, vol. 20, No. 1, Jan. 1994, pp. 1 & 3.

Sutliff, Jacqueline, "Detecting Drugs in Perspiration", Technical Bulletin of PharmChem Laboratories, Inc., vol. 3, No. 2, Summer 1993 (2 pages).

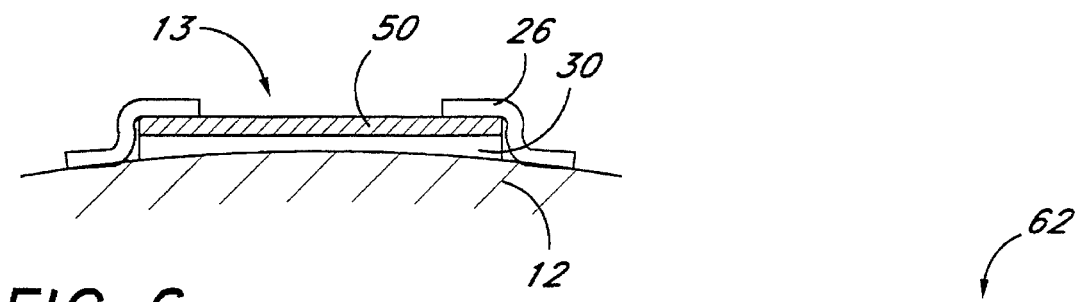
FIG. 6
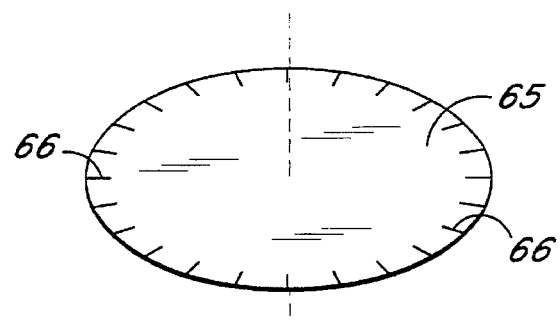
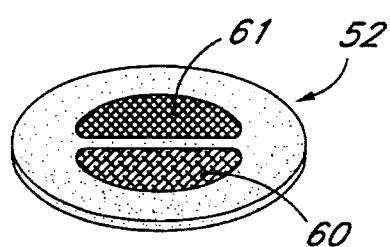
FIG. 7
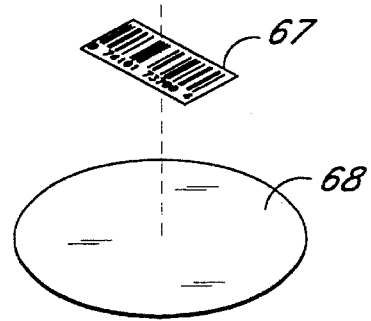
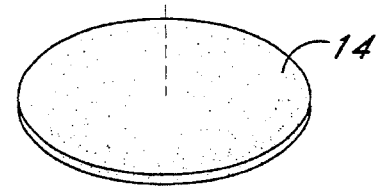
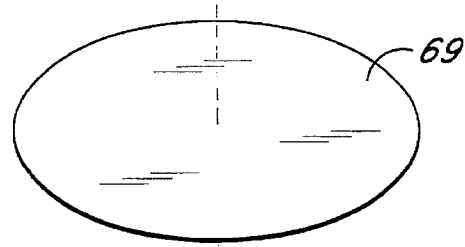
FIG. 8

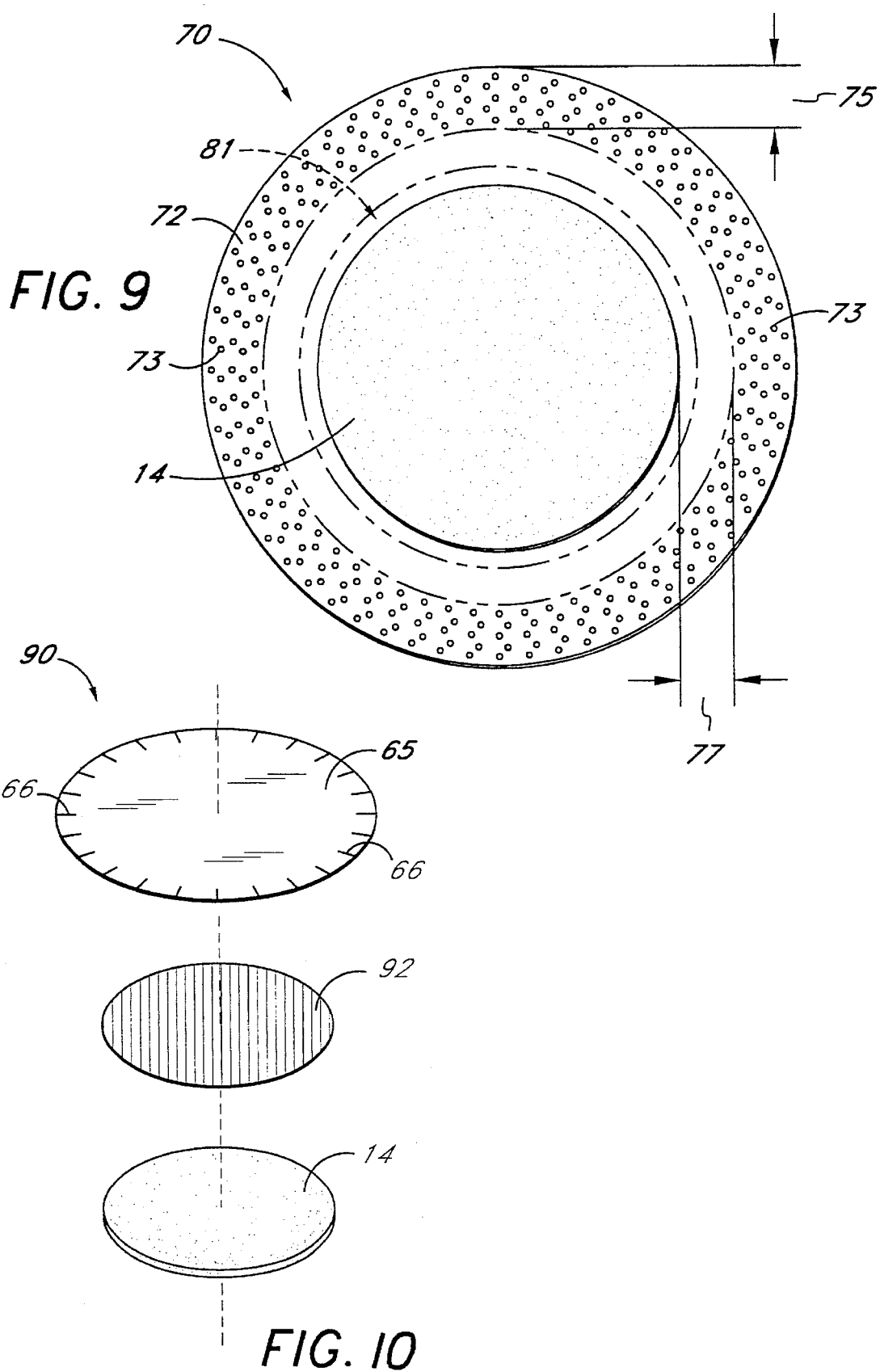

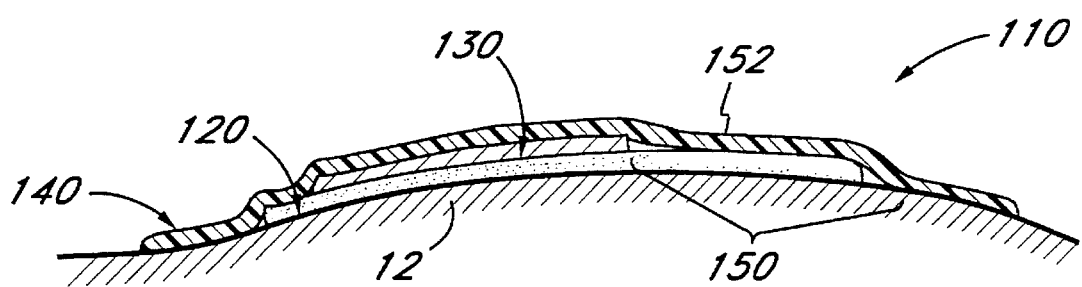
FIG. II

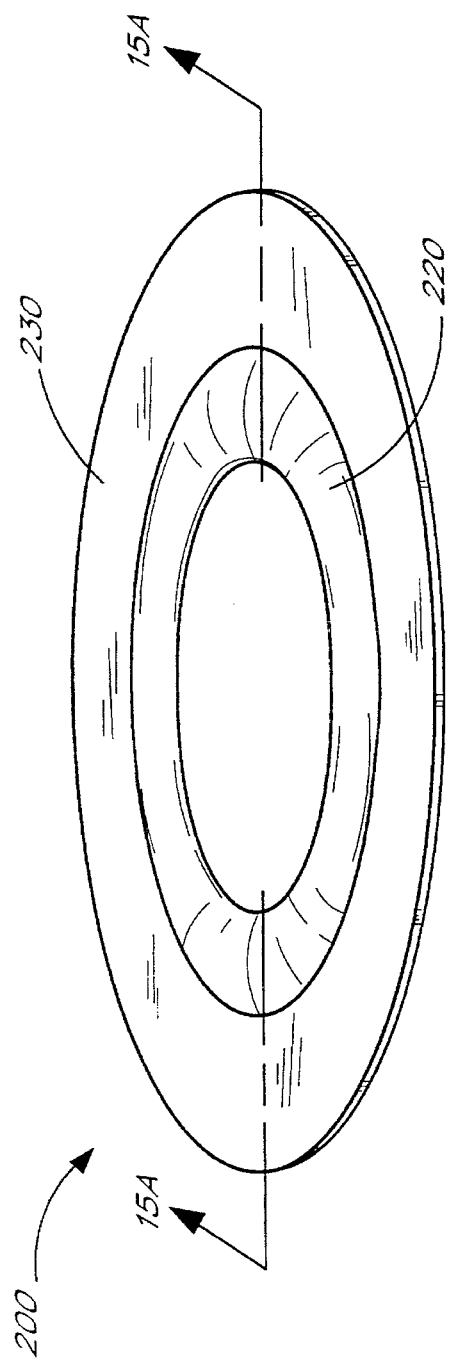
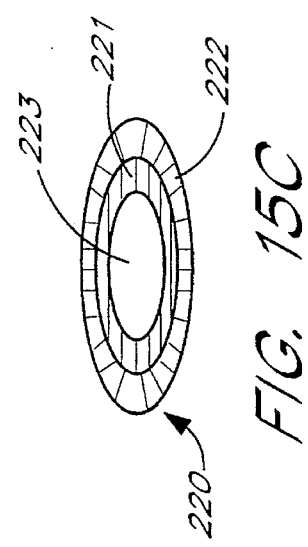
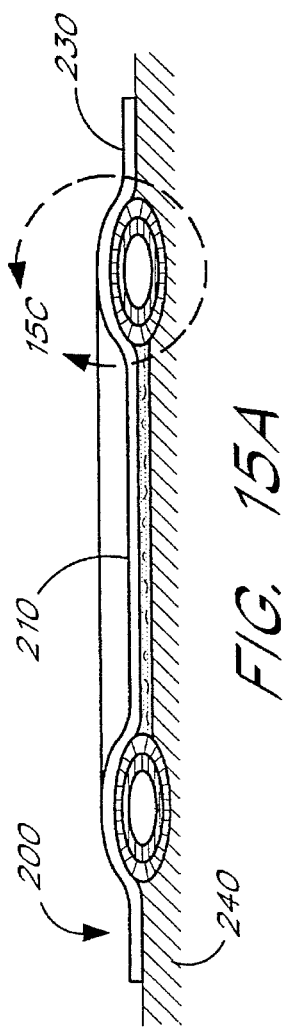
FIG. 15B
FIG. 15C
FIG. 15A

ENERGY-ASSISTED TRANSDERMAL COLLECTION PATCH FOR ACCELERATED ANALYTE COLLECTION AND METHOD OF USE

RELATED APPLICATIONS

The present application is a continuation-in-part of U.S. application Ser. No. 08/039,631, filed Mar. 30, 1993, which is a continuation in part of Ser. No. 989,204, filed Dec. 11, 1992, which is a continuation-in-part of Ser. No. 569,007, filed Aug. 15, 1990, which is a continuation-in-part of application Ser. No. 241,707, filed Sep. 8, 1988, now U.S. Pat. No. 4,957,108. The disclosures of these previous applications are hereby incorporated herein in their entirety by this reference thereto.

FIELD OF THE INVENTION

The present invention relates to derreal patches which employ heat generating means to induce perspiration in a subject so that analytes present in such perspiration can be collected in a dermal patch and detected. The present invention also relates to methods of using such patches.

BACKGROUND OF THE INVENTION

A. Inducing Perspiration

Early investigators of the components of perspiration used various means to increase the quantity of perspiration which they could collect from subjects and thereafter analyze. One such means of inducing perspiration involved placing rubber gloves over the hands of a subject. When perspiration accumulated on the subject's hands, it was collected for analysis (U.S. Pat. No. 3,552,929 to Fields, et al.).

Chemical means have also been developed to accelerate the collection perspiration. For example, perspiration-inducing chemicals such as pilocarpine have been administered to increase perspiration. One way of administering these chemicals is to iontophorese them into the skin (Gibson, *Pediatrics*, 23:545, 1959). Permeation-enhancing chemicals, used in conjunction with abrasion to the skin, have also been employed (see, e.g., U.S. Pat. No. 4,756,314 to Eckenhoff, et al.)

Heat has been used as well in connection with the detection of analytes under the skin and with the transport of substances into a subject's body through the skin. In U.S. Pat. No. 4,401,122, Clark describes a method of arterializing the skin of a subject with heat or other means. Clark specifies that a subject's skin can be heated to 38°–44° C. in order to control a chemical reaction beneath the skin or in order to accelerate diffusion through the skin. Jacques, et al. (in U.S. Pat. No. 4,775,361) also describe the use of pulsed laser energy to enhance percutaneous transport.

B. Perspiration and Other Diagnostic Media

As the result of the collection and analysis of perspiration, it has been found that perspiration contains a variety of analytes of interest. In order to detect such analytes, a sufficient quantity of perspiration must first be collected from a subject so that the perspiration can be subjected to analysis. Prior art dermal patches were normally maintained on the skin of a subject for 24 hours in order to collect sufficient perspiration (see, e.g., U.S. Pat. No. 4,706,676 to Peck and U.S. Pat. Nos. 4,732,153 and 4,329,999 to Phillips). The result of using this method of collecting an analyte is a longterm integration of the concentration of the analyte in the subject's perspiration over the wear period. Specific information as to when the analyte was in the body or whether the patch was exposed to one large or multiple smaller amounts of the analyte is lost in such long-term wear.

Other diagnostic media can reveal different information regarding the concentration of an analyte. For example, the analysis of a venous blood sample reveals the concentration of an analyte in the venous circulatory system at the instant that the sample is taken. A urine sample, on the other hand, contains information as to an analyte's concentration that is somewhere in between the instantaneous information of a blood sample and the time-averaged information available from derreal patches. A urine specimen is representative of the concentration of an analyte in the body between complete voids, so that the higher the frequency of voids is, the closer the urine specimen will represent the instantaneous situation.

C. Diagnostic Kits for Collecting Perspiration

A variety of diagnostic kits for monitoring an analyte in perspiration have been developed. For example, U.S. Pat. No. 3,552,929 to Fields, et al. discloses a BAND-AID type test patch suited for determining the chloride ion concentration in perspiration as a method of diagnosing cystic fibrosis. The apparatus disclosed in Fields comprises an absorptive perspiration collecting pad with an impermeable overlying layer for the purpose of preventing evaporation. When the absorptive pad is saturated, the patch is removed from the skin and exposed to a series of strips impregnated with incremental quantities of silver chromate or silver nitrate, the color of which undergoes a well known change upon conversion to the chloride salt.

U.S. Pat. No. 4,706,676 to Peck discloses a dermal collection device which comprises a binder to prevent reverse migration of an analyte, a liquid transfer medium which permits transfer of an analyte from the derreal surface to the binder, and an occlusive cover across the top of the liquid transfer medium and binder. Peck also discloses the application of such a dermal collection device to detect various environmental chemicals to which humans are exposed. After the derreal collection device has been worn on a patient's skin for a period of time, the device is removed for analysis, which involves the chemical separation of the bound substance of interest from the binding reservoir and thereafter undertaking qualitative and/or quantitative measurement of the substance of interest by conventional laboratory techniques.

Another derreal collection device, disclosed in U.S. Pat. No. 4,756,314 to Eckenhoff, claims to quantitatively collect perspiration on a dermal patch. This patch uses a diffusion rate-limited membrane as a means to maintain a constant flow of fluid into the patch. The patch comprises an impermeable outer boundary structure, and is therefore an occlusive patch.

However, prior art derreal patches and other means of collecting perspiration are generally only useful for determining the presence of analytes which are present in perspiration in relatively high concentrations, such as halide ions. In addition, the occlusive outer layer-type devices of the prior art are susceptible to the problem of back diffusion of perspiration and/or the analytes contained therein. Occlusive devices also suffer from other problems, including changes in the skin's transport characteristics (see, Brebner, D. F., *J. Physiol.*, 175:295–302 (1964) and Feldmann, R. J., *Arch. Dermat.*, 91:661–666 (1965)), and the maintenance of an aqueous state below the patch, which fosters bacterial growth. Prior art dermal patches suffer from a number of other disadvantages as well, including being uncomfortable to wear and being subject to losing analytes due to fluid loss.

SUMMARY OF THE INVENTION

In one aspect of the present invention, the invention comprises a method of collecting an analyte contained in the perspiration of a mammal through the use of a dermal patch. This method comprises the steps of:

(a) placing a dermal patch on the skin of a mammal, wherein the patch comprises an absorbent material for collecting analytes contained in the perspiration of the mammal;

(b) heating the skin of the mammal underneath the dermal patch, wherein sufficient heat is generated to cause a flow of perspiration through the skin of the mammal;

(c) collecting an analyte present in the perspiration of the mammal in the absorbent material of the patch;

(d) removing the patch after a sufficient period of time has elapsed following the initial application of heat to the skin of the mammal to allow the analyte to be detected in the patch by an assay for the analyte; and (e) detecting the presence of the analyte in the patch. In the foregoing method, step (b) can, for example, comprise generating heat by means of a chemical reaction. In this embodiment, the chemical reaction can be produced by means of a chemical composition which reacts exothermically in the presence of oxygen. Step (b) would involve exposing the chemical composition to oxygen in such an embodiment. In an alternative embodiment, step (b) can comprise generating heat with an electrical device such as an electric heating pad. In this embodiment, the heating pad can be placed on top of the dermal patch.

In heating the skin of the mammal according to step (b) of the foregoing method, the temperature of the skin of the mammal should be raised to between about 100° F. and 150° F., and preferably to between about 105° F. and 115° F. The skin of the mammal underneath the dermal patch can also be heated by raising the internal body temperature of the mammal. The patch should be removed according to step (d) of this method after between 1 and 2 hours, and more preferably after about 1 hour. However, the patch may also be removed according to step (d) after less than 1 hour.

The foregoing method can be advantageously used to detect drugs of abuse. Thus, in one embodiment, step (e) of this method can comprise detecting the presence of cocaine in the patch which is used in this method.

Another aspect of the present invention is an improved apparatus for detecting an analyte contained in the perspiration of a subject mammal. This apparatus includes, first of all, a dermal patch. This patch further comprises:

a) an outer protective layer having an adhesive applied to one side of the layer, the adhesive being adapted to secure the outer protective layer to the skin of a subject mammal; and b) an absorbent material for collecting analytes contained in the perspiration of the subject, wherein the absorbent material is secured to the side of the outer protective layer to which the adhesive is applied, the absorbent material being in fluid communication with the skin of the subject when the patch is worn on the subject's skin.

The foregoing apparatus further includes an electric heater overlying the absorbent material and/or overlying the outer protective layer of the patch, so that the heater can generate heat on the surface of the skin of the subject. This heater should be capable of reaching temperatures in excess of 105° F. In one embodiment, the electric heater can be a heating pad. The electric heater can alternatively be an electrically conductive heating element in the patch.

Yet another aspect of the present invention comprises a single use dermal patch for detecting an analyte contained in the perspiration of a subject mammal. In this aspect of the invention, the patch comprises:

a) an outer protective layer having an adhesive applied to one side of the layer, the adhesive being adapted to secure the outer protective layer to the skin of a subject mammal;

b) an absorbent material for collecting analytes contained in the perspiration of the subject, wherein the absorbent material is secured to the side of the outer protective layer to which the adhesive is applied, the absorbent material being in fluid communication with the skin of the subject when the patch is worn on the subject's skin; and c) a chemical composition which can undergo an exothermic chemical reaction and thereby produce heat, wherein the composition is secured to the outer protective layer or to the absorbent material of the patch, and wherein the composition is capable of reaching temperatures in excess of 105° F. when reacted.

The chemical composition used in this patch should be one which reacts exothermically when exposed to air. For example, the composition can comprise iron, a metal chloride or metal sulfate, activated carbon, and water. In this embodiment, the patch should be packaged in a material that is resistant to the influx of air. More preferably still, the composition used in this patch can be further contained in a porous bag in the patch. In a particular embodiment of a patch according to this aspect of the present invention, the chemical composition can be present in the patch around a periphery defined by the edges of the absorbent material of the patch.

BRIEF DESCRIPTION OF THE FIGURES

FIG. 1 a is a cross-sectional view along the line 1a—1a of the derreal patch of FIG. 1.

FIG. 6 is a cross-sectional view of a dermal patch according to a further embodiment of the present invention.

FIG. 7 is a plan view of a derreal patch according to another embodiment of the present invention.

FIG. 8 is an exploded elevational view of a dermal patch according to yet another embodiment of the present invention.

FIG. 9 is a plan view of a dermal patch according to a further embodiment of the present invention.

FIG. 10 is an exploded elevational view according to still another embodiment of the present invention.

FIG. 11 is a cross-sectional view of a dermal patch of the present invention which includes a pooling area.

FIG. 15A is a cross-sectional view of one embodiment of an energy-assisted dermal patch according to the present invention.

FIG. 15B is a view of the top of the patch of FIG. 15A when such a patch is present on the skin of a subject.

FIG. 15C is a cross-sectional view of the chemical composition and bag layers shown in FIG. 15A.

DETAILED DESCRIPTION OF THE INVENTION

I. Dermal Patches for Detecting Analytes

A. Non-Occlusive Dermal Patches

Figure 1:
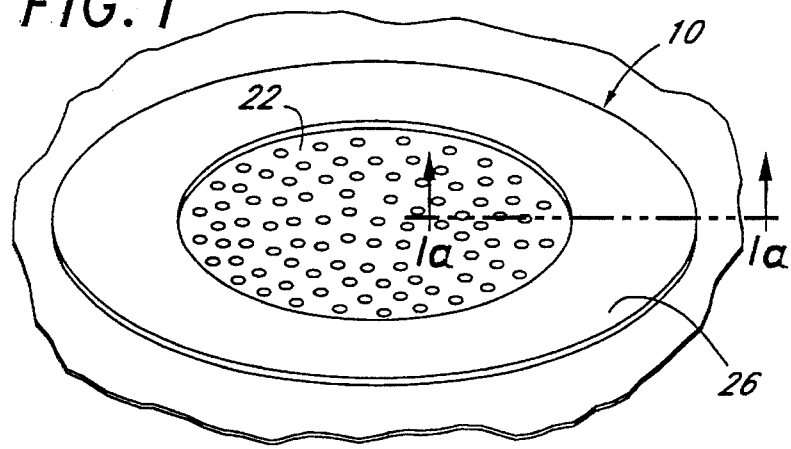
FIG. 1 is a perspective view of a derreal patch according to one embodiment of the present invention.

Referring to FIG. 1, there is disclosed a dermal patch 10 according to one embodiment of the present invention, illustrated as being secured to the surface of the skin 12 of a subject. As will be appreciated by one of skill in the art, the patch of the present invention may be used for veterinary purposes as well as on humans. In addition, the patch can be used in more diverse applications such as in agriculture or any other environment where a chemical species is to be detected in a fluid. The preferred use, however, is for determination of preselected chemical species or analyte in sweat (perspiration), and the ensuing discussion is principally directed to that use.

Moisture expressed from the skin 12 within the perimeter of the test patch 10 first accumulates in a concentration zone 14 beneath the first side of a gas permeable filter or layer 16 which is in fluid communication with the skin 12. The concentration zone 14 preferably contains an absorbent material, such as a fluid permeable medium 20 which may be cotton gauze or other commonly available fluid permeable material. For example, a layer of any of a variety of known fiber webs such as knitted fabrics, or nonwoven rayon or cellulose fibers may be used. Filtration Sciences #39 is a particularly preferred fluid-permeable medium for use as a concentration zone in the present invention. In a preferred embodiment, the absorbent material contains binders, such as antibodies, for specifically binding analytes of interest to the absorbent material of the patch. As used herein, the term "absorbent material" designates any fluid permeable material capable of collecting or holding analytes contained in perspiration. Preferably, such a material is also able to concentrate such analytes on the patch.

The term "fluid permeable" is used herein to describe a material which will permit the passage of the liquid phase of fluids expressed from the skin and which will also allow the passage of the vapor phase of such fluids. A fluid permeable filter or layer will thus allow the passage of water in both the liquid and vapor phases. "Water" is used herein to denote both the liquid and vapor phases of water unless reference is specifically made to a particular phase.

Moisture from perspiration accumulates in the interfiber spaces of the medium 20. Under the influence of body heat which is readily conducted from the surface of the skin through the liquid phase, the liquid water component of the perspiration will tend to volatilize. Such volatilized water can thereby pass through the gas permeable filter or layer 16, which is located on the side of the medium 20 distal of the skin 12, and leave the patch 10.

As previously discussed, the patch 10 is provided with a gas permeable filter 16. The term "gas permeable" is used to describe a material which permits the passage of gases, including the vapor phase of fluids expressed from the skin, but substantially retains the fluid phase within the patch. Any of a variety of suitable commercially available microfiltration membrane filters may be used for this purpose, such as the Gore-Tex 0.45 micron Teflon filter manufactured by W. L. Gore & Associates, Inc. (Elkton, Md.).

Adjacent a second side of the gas permeable filter 16 is a discharge zone 18. As previously discussed, the gas permeable filter 16 retains the fluid phase but permits escape of the vapor phase of the fluid component in perspiration. Thus, the vapor component, which primarily consists of vaporized water, continuously escapes through the gas permeable filter 16 exiting the second side thereof into discharge zone 18, which is in communication with the atmosphere. In an alternative embodiment, not separately illustrated, the gas permeable filter 16 is replaced by a fluid permeable membrane which permits passage of the liquid phase. In this embodiment, liquid, or a combination of vapor and liquid, will be permitted to escape from the patch. Any of a variety of fluid permeable filters are commercially available which can be used to form a fluid permeable filter used in this embodiment of the present invention. A preferred fluid permeable filter is constructed from James River Paper Drape.

A flexible, gas permeable outer layer 22 is preferably disposed adjacent the second side of filter 16 in the discharge zone 18. This layer serves to protect the filter 16 against physical damage such as abrasion, and can also serve as a barrier for preventing chemical contamination of the filter material from the outside. Outer layer 22 may comprise any of a variety of commercially available gas permeable tapes and films which are known to one of skill in the art. Outer layer 22 may also be distinct from or integral with tape 26, discussed below. Alternatively, depending upon the intended application of the patch, outer layer 22 may be deleted altogether, where it does not appear that abrasion or external contamination will deleteriously affect the patch 10, or where the gas permeable layer 16 is made from a material which is itself resistant to abrasion and/or external contamination, thus obviating the need for the outer layer 22.

The patch 10 illustrated in FIG. 1 is secured to the surface of the skin by means of a peripheral band of tape 26. Preferably, the tape 26 will extend around all sides of the patch 10. For example, an annular ring of tape can be die punched for use with a circular patch, or the center of a rectangular piece of tape can be removed to expose outer layer 22 or filter 16 of a rectangular patch (see FIGS. 1 and 3, respectively). Alternatively, outer layer 22 and tape 26 can be deleted altogether and layers 16 and 20 can be secured to the surface of the skin by a bandage or through the use of an adhesive. One such method would be to capture layers 16 and 20 under a bandage or wrapping surrounding the arm or the leg. In this case, the gases and/or fluids are permitted to escape through layers 16 and 20 and into the bandage, where they may either collect or from which they are dissipated into the environment.

A large variety of hypoallergenic or other suitable tapes are well known in the art, which may be adapted for use with the patch 10 of the present invention. Different tapes or adhesives may be desirable depending upon the intended use of the test kit, based upon their ability to adhere to the skin during different conditions such as daytime wearing under clothing, during sleep, during profuse sweating for prolonged periods or during showers. It has been determined that the most desirable tapes include multiple perforations which prevent sweat from building up underneath the tape and eventually compromising the integrity of the adhesive. Preferably, a tape, such as Dermiclear marketed by Johnson & Johnson, is used. More preferably, the tape comprises a layer of 3M 1625 Tegaderm wound dressing available from the 3M Company (St. Paul, Minn.).

Any of a wide variety of means for securing the patch 10 to the skin 12 may be utilized. For example, the tape 26 can be eliminated and gauze layer 20 provided with a lower adhesive layer to perform the same function. One such adhesive membrane is the MN-100 adhesive membrane manufactured by Memtec of Minnetonka, Minn. This membrane is fluid permeable so that it passes fluid as would the gauze layer 20, yet has one adhesive side so that it will stick to the skin. Alternatively, outer protective layer 22 can comprise an annular flange 23, extending radially outwardly beyond the outer edges of filter 16 and gauze 20 (see FIG. 2a). The lower surface of the flange 23 is then provided with a suitable adhesive.

The surface temperature of human skin varies regionally. However, it is generally within the range of from about 86° F. to about 90° F. at rest, and can rise to much higher temperatures under conditions of strenuous exertion. At those temperatures, a number of chemical species of interest for the purpose of the present invention, such as creatine kinase or a high or low density lipoprotein, have a sufficiently low vapor pressure that volatilization is not a significant factor in the efficiency of the concentration function. At the same time, the substantial aqueous component will have a sufficiently high vapor pressure that it will tend to volatilize, thereby concentrating the less volatile fractions. However, in some applications the chemical species of interest will have a high enough vapor pressure, even at the resting temperature of human skin or the temperature of another surface to which a patch of the present invention is applied, such that escape of the vapor phase through the gas permeable filter 16 of the analyte of interest will disadvantageously impair the efficacy of the test patch. For these analytes, a modified patch must be used.

B. Dermal Patches for Detecting Volatile Analytes

Figure 2:
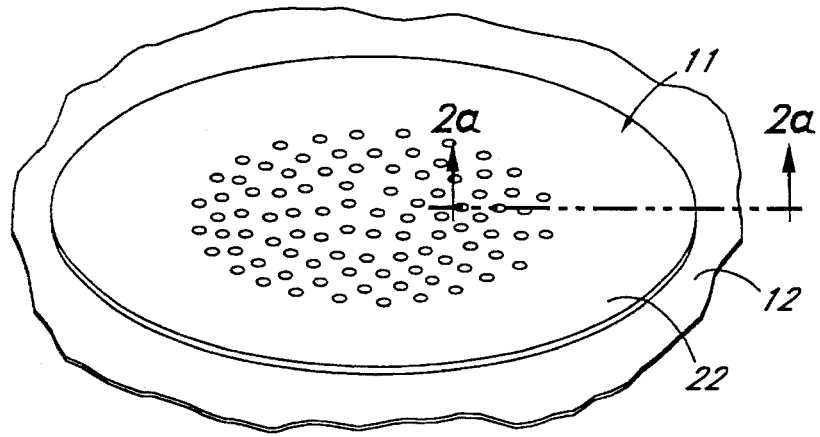
FIG. 2 is a perspective view of a dermal patch according to a second embodiment of the present invention.
Figure 2A:
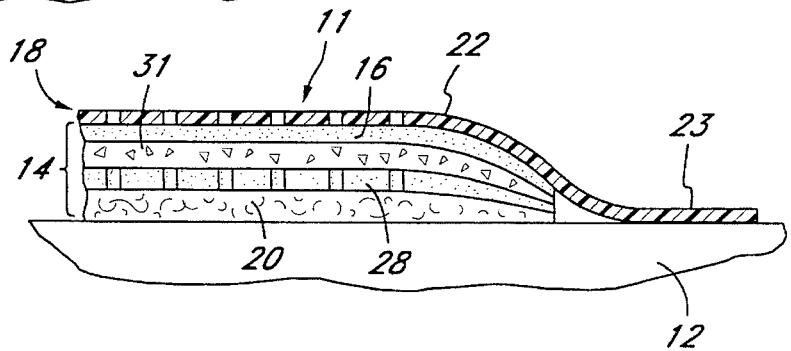
FIG. 2a is a cross-sectional view along the line 2a—2a of the dermal patch of FIG. 2.

Referring to FIGS. 2 and 2a, there is disclosed a modified patch 11 according to the present invention for use in detecting an analyte having a propensity to escape through the gas permeable filter 16 as a vapor under ordinary use conditions. The test patch 11 comprises a concentration zone 14 defined on its inner boundary by the skin 12 to which the patch 11 is secured. The outer boundary of the concentration zone 14 is defined by the gas permeable filter or layer 16, which separates the concentration zone 14 from the discharge zone 18. Disposed in the concentration zone 14, and adjacent the gas permeable filter 16, is a binder layer 31 for binding and preventing the escape of molecules of the volatile analyte. The binder layer 31 is separated from the gauze layer 20 by a porous layer 28, which may compromise any of a variety of films for retaining the binder layer 31 yet permitting passage of fluid.

In the embodiment illustrated in FIG. 2a, perspiration will pool in the interfiber spaces of the gauze 20, and will percolate through porous layer 28 into the binder layer 31. In that layer, a chemically active or biochemically active binder material will act to selectively bind the volatile analyte, thereby preventing it from escaping as a vapor through gas permeable filter 16. As discussed in connection with the embodiment illustrated in FIG. 1, it is also possible to replace the gas permeable filter 16 with a fluid permeable layer, where the presence of fluid on the outside of the test patch would not be undesirable.

The binder layer 31 may comprise any of a variety of binders depending upon the nature of the volatile analyte to be determined. For example, the binder may chemically bind with the analyte or adsorb the analyte to be determined. Thus, when the analyte being collected is ethanol, the binder layer advantageously contains activated charcoal. In addition, the binder layer may comprise a specific binding partner of the analyte to be determined, such as a polyclonal or monoclonal antibody or an antigen matched to a specific antibody desired to be measured in the perspiration.

The patch 11 is additionally provided with tape 26 or another means for securing the patch to the skin of a subject, as has been detailed in connection with the embodiment illustrated in FIG. 1. Patch 11 is illustrated, however, as having a unitary outer layer 22 extending beyond the perimeter of the underlying layers to form an annular flange 23, which is provided with an adhesive on its lower surface. As discussed in connection with the embodiment of FIG. 1, outer protective layer 22 permits the escape of water vapor yet protects the filter material from chemical contamination from the outside. As also discussed above, gas permeable layer 16 can also in some cases function as the outer layer 22.

C. Dermal Patches Having a Microbead Layer

Figure 3:
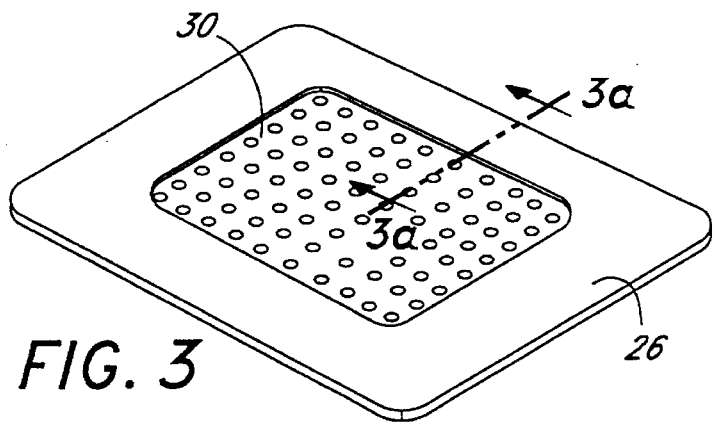
FIG. 3 is a perspective view of a third embodiment of the dermal patch of the present invention.
Figure 3A:
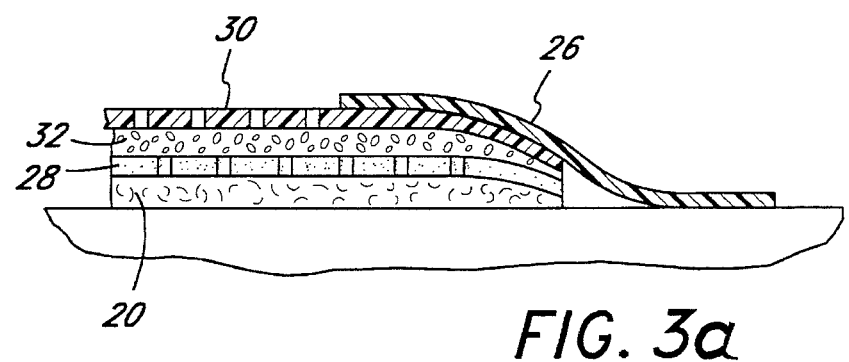
FIG. 3a is a cross-sectional view along the line 3a—3a of the patch of FIG. 3.

Referring to FIGS. 3 and 3a, there is disclosed a further embodiment of the test patch of the present invention wherein an inner porous layer 28 and an outer porous layer 30 define a space for containing a microbead layer 32. The microbeads of such a microbead layer 32 can desirably have attached thereto a capture reagent, such as antibodies or other means for binding analytes of interest. The inner layer 28 and outer layer 30 preferably comprise the same material, which may be any suitable material for providing an unrestricted flow of fluid through the patch while trapping the microbeads in between. One suitable material for porous layers 28, 30 is the fluid permeable and microporous film known by the name Ultipor (nylon 6) and manufactured by Pall Corporation in Glen Cove, N.Y. Additional manufacturers of suitable nylon filtration membranes include Micron Separations, Inc. of Westborough, Mass., and Cuno of Meridan, Conn. Porous layers 28, 30 may also be comprised of materials other than nylon, such as polycarbonate, modified polyvinylchloride and polysulfone.

The gauze, the inner and outer porous layers and the adhesive tape in all embodiments can be cut to size with conventional dies. The gauze 20 and the inner porous layer 28 can be fixed to the adhesive ring 26 with conventional adhesives, such as those used on the adhesive surface itself. Alternatively, they could be heated or ultrasonically bonded together. The proper amount of microbeads can then be placed on top of the inner porous layer, after which the outer porous surface is attached by similar means. Typically, in a one-inch diameter patch, from about 0.05 grams to about 1 gram of microbeads will be used, and preferably from about 0.1 to about 0.4 grams will be used. The inner and outer porous surfaces may have to be staked or spotwelded together in some pattern, as will be appreciated by one of skill in the art, to prevent the microbeads from collecting in one area.

The free adhesive surface is optimally covered by pull-away paper (not illustrated) with adequate space to be gripped with one's fingers. The patch is packaged in a paper or plastic pouch similar to that used in conventional band-aid packaging. The assembled unit could be terminally sterilized or pasteurized prior to sale. Alternatively, the package could comprise a vapor barrier such as a metallic foil or mylar and even include oxygen or moisture absorbent means such as a small packet of any of a variety of known desiccants, such as silica gel, calcium chloride, calcium carbonate, phosphorous pentoxide or others as will be appreciated by one of skill in the art.

The total thickness of microbead layer 32 can be varied considerably. However, if a color change is to be used to detect an analyte and the such color change is to be brought about by immersing the patch in appropriate reagent baths, layer 32 is preferably no more than about 3 mm thick since color changes occurring at immobilized sites on thicker layers would not likely be observable. More preferably, the microbead layer is between about 1 mm and about 2 mm thick. If such color change analysis is not performed, the microbead layer 32 can alternatively be torn open, releasing loose microbeads which can be used to conduct chemical analysis for detecting the presence of an analyte bound to the microbeads by conventional means, such as in a cuvette.

Optimally, the diameter of the beads in microbead layer 32 will be at least about one order of magnitude larger than the diameter of the pores in inner porous layer 28 and outer porous layer 30. For example, the beads contained in microbead layer 32 may have diameters within the range of from about 5 to 50 microns, and preferably within the range of from about 5 to about 10 microns. If 10-micron diameter beads are utilized in the microbead layer 32, for example, inner porous layer 28 and outer porous layer 30 will optimally comprise a median pore size of approximately 1 micron.

The microbead layer 32 may comprise any of a variety of known materials including polystyrene, latex, and glass. Beads sized from approximately 0.05 micron to 100 micron which are suitable for the present application are available from Polysciences of Warrington, Pa.

Microbead layer 32 serves as the support for an immobilized specific binding partner for the analyte to be determined. Thus, a molecule with a high chemical affinity for a specific component in the fluid to be analyzed will be immobilized to the microbeads in microbead layer 32.

D. Dermal Patches Having an Impermeable Outer Layer

Figure 5:
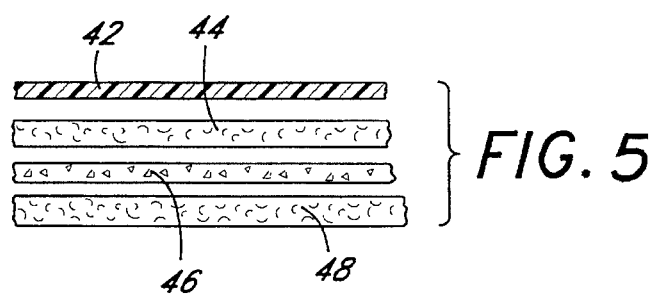
FIG. 5 is an exploded elevational schematic view of a fourth embodiment of the present invention.

Referring to FIG. 5, there is disclosed a further embodiment of the present invention, particularly suited for use under conditions in which profuse sweating is not present, such as in passive insensible perspiration, wherein the test patch is provided with an impermeable outer layer 42. In order to minimize any back diffusion of fluid into the skin, an absorptive layer 44 is provided to form a reservoir for drawing moisture away from the surface of the skin and through support 46 to which is bound a specific binding partner for at least one analyte to be determined. Layer 44 may include chemical means for binding or collecting moisture such as a desiccant, as has been previously discussed, which is suitable for use in proximity to the skin. The patch may be further provided with an underlying porous layer 48 to separate support 46 from the surface of the skin, and the patch is provided with any of the means for attachment to the skin as have been previously discussed.

E. Derreal Patches which Minimize Lateral Diffusion of Sweat in a Patch

Referring to FIG. 6, there is disclosed a modified patch 13 according to the present invention, in which all intervening layers between the skin 12 and the binder layer 30 have been deleted. By disposing the binder layer (i.e., the layer having a specific binding partner for an analyte to be determined) directly adjacent the skin, lateral diffusion of sweat throughout the binder layer 30 is minimized. The proximity of the binder layer 30 to the skin 12 allows the output of each duct of the sweat glands to contact or be in fluid communication with a relatively small area of the binder layer 30. For a variety of reasons which will be apparent to one of skill in the art, it may also be desired to mount a microporous membrane, preferably a fluid permeable membrane 50 atop the binder layer 30.

The evaporative capacity of the binder layer 30 and the fluid permeable membrane 50 is preferably sufficient relative to the output capacity of the individual sweat ducts, to minimize lateral diffusion of sweat away from the immediate area of the duct. This embodiment has special application for monitoring the chemical composition of insensible perspiration and/or non-exercise perspiration, in instances where output from the sweat glands is limited. Due to the magnification effect detailed infra, the present embodiment is also particularly suited for monitoring low concentration analytes.

By limiting the suppressive characteristics of moisture or water on the skin, through the use of materials having a maximal evaporative capacity, the instant embodiment allows increase of the through-put rate of sweat in the patch by maximizing sweat gland output. Nadel and Stolwijk, *J. Applied Physiology*, 35(5): 689–694 (1973), disclose that sweat gland activity is suppressed by water lying on the skin, finding a difference in whole body sweat rate of 40% between wet and dry skin. Mitchell and Hamilton, *Biological Chemistry*, 178:345–361 (1948), found that loss of water and solutes in insensible perspiration presumably stops whenever the surface of the skin is covered with a film of water. Brebner and Kerslake, *J. Physiology*, 175:295–302

(1964), postulate that the reason for this phenomenon is that water in contact with the skin causes the epidermal cells of the skin to swell and thus block the sweat ducts.

The ability of the present invention to produce a positive response based upon the presence of relatively low concentrations of analyte is particularly advantageous in view of the fact that, during active exercise, a ¼' diameter area of skin provides approximately 35 microliters of sweat per hour, whereas a similar diameter area of skin produces sweat at a non-exercise rate of only about 3.2 microliters per hour. The present embodiment is further advantageous as not requiring the user to exercise, but only to wear the patch for an equal or typically longer period during rest or at normal activity levels.

Thus, homogeneous diffusion of sweat throughout the binder layer is preferably minimized when using the instant invention in conjunction with insensible and/or non-exercise perspiration and/or a determination of minute amounts of analyte contained within perspiration. The minimized lateral diffusion of perspiration throughout the binder layer 30, according to the present invention, provides a more concentrated collection of sweat at each sweat duct, thereby providing a greater amount of selected analyte to be determined at that area.

F. Dermal Patches Having Multiple Test Zones

Referring to FIG. 7, there is shown a modified binder layer 52 for a patch according to the present invention, wherein two or more distinct zones are provided on the binder layer 52. The use of a reference zone or of several distinct test zones is contemplated for both the single layer patch discussed in connection with FIG. 6, as well as the embodiments discussed in connection with FIGS. 1–3a and 5. The multizone binder layer 52 may also be used for certain embodiments to be discussed hereinafter in connection with FIGS. 6–10 when specific binding chemistry is used.

One or more of the zones, such as determination zone 60 (FIG. 7), is used to test for an analyte of interest within sweat, as detailed previously. One or more of the remaining zones, such as reference zone 61, is used as a reference indicator.

Reference zone 61 performs a variety of functions, depending upon the desired application of the test patch. For example, reference zone 61 can be provided with color change chemistry as discussed previously to provide the wearer with an indication that the patch has been worn for long enough that a sufficient sample volume has traversed the patch to provide a meaningful test for the analyte of choice. For this purpose, reference zone 61 is provided with affinity chemistry for a preselected reference substituent such as IgG, albumin or any other sweat component which is reliably present. Preferably, the selected reference substituent is one which provides a reasonably accurate measurement of the volume of sweat put through the system.

This use of the reference zone 61 may be facilitated by first determining the rough concentration ratio of a reference substituent such as albumin to the analyte to be determined and providing the patch with color change chemistry which provides a visual indication of the presence of the reference substituent only well after the elution of the analyte to be determined has exceeded the lower limits of detection. Reference substituents such as albumin will typically be present in significantly greater quantities than the analyte. Thus, in order to accomplish the objective of indicating passage of a sufficient sample volume, the "sensitivity" of the patch for the reference substituent is preferably lower than for the analyte. This can be achieved by using a proportionately lower amount of a specific binding partner for the reference substituent than for the analyte, other dilutions in the assay, or simply selecting a less abundant reference substituent. Selection of a suitable reference substituent and concentration determinations can be readily made through simple experimentation by one of skill in the art.

G. Use of Dermal Patches Having Multiple Test Zones to Prevent Tampering

Alternatively, and particularly useful in assays for drugs of abuse and their metabolites, a reference zone 61 (FIG. 7) can provide an indication that the skin patch was actually worn by the desired patient, parolee or other subject. One inherent limitation in a test in which a subject desires a negative result is the possibility that the subject will simply remove the patch after administration and replace it just prior to reexamination. This possibility gives rise to the ability of the wearer to ensure false negative results.

However, by provision of a reference zone 61 to detect a known component in sweat, the test results will reveal test patches that have not been worn for the test period. Reference zone 61 thus provides a method of preventing false negative evaluations due to tampering or removal of the test patch.

A reference zone 61 to detect a known component in sweat may also be provided as a positive control zone to ensure the discovery of false negative test results due to degradation of reagents or other components of the patch. In non drug-of-abuse screens, the indication produced within the reference zone 61 will preferably be a visible color change by a chemical or antibody/antigen colorimetric interaction occurring or becoming apparent to the wearer when a predetermined amount of the reference analyte has passed through the interaction area.

Optionally, a reference zone 61 may be provided as a negative control zone to enable the discovery of false positive results. A preferred negative control zone will have an immobilized specific binding partner for an analyte known to be absent in human sweat. The analyte's specific binding partner must be known to not cross react with components present in human sweat. An example of an appropriate analyte is bacteriophage T4 coat protein.

In yet a further embodiment of the present invention (not illustrated) two or more analyte determination zones 60 are provided in a single test patch. The use of multiple test zones is particularly useful in applications such as a drug of abuse screen where testing for any one or more of a wide variety of analytes may be desired. For example, a single test patch may be used to screen for any of a plurality of drugs of abuse, such as THC, Phencyclidine morphine and Methadone. A positive result for any of the drugs on the screen may provide sufficient proof of an offense such as a violation of parole, or can be used to signal the need for more quantitative follow up investigations. Used as an initial screening tool, the present invention offers the advantages of being non-invasive, and much less expensive than conventional quantitative analyses. For these reasons, a screening test patch as disclosed herein is particularly suited for initial screening of large populations such as parolees, inmates, military personnel or others where monitoring is desired.

The analyte determination zone 60 and analyte reference zone 61 may be physically separated on the patch, such as in concentric circles or discrete zones, as illustrated in FIG. 7, or in the case of only two or three analytes, interspersed throughout. In the latter case, positive results of different determinations would be indicated by the appearance of different colors.

II. Placement of Derreal Patches

Although a patch of the present invention can be used to collect analytes contained in any of a variety of body fluids, perspiration is the desired fluid to be collected due to its dependable supply and its similarity to blood, albeit with lower analyte concentrations. Although components found in saliva could also be collected with a patch of the present invention, saliva is often contaminated with molecules not expressed by the body, such as foodstuffs. Therefore, in a preferred embodiment, the patches of the present invention are placed on the skin surface of a subject.

A. Characteristics of Sweat Glands and Perspiration

Sweat glands are classified to be either of two types. Eccrine type sweat glands function primarily to regulate body temperature through their relationship to evaporative heat loss. It is the eccrine type sweat gland that provides the sweat associated with exercise and is therefore the source of perspiration of interest for many applications of the patch of the present invention. Apocrine type sweat glands are larger secreting elements which are localized only in relatively isolated areas of the body such as the axilla, pubic and mammary areas.

Sato and Fusako, *American J. Physiology*, 245(2): 203–208 (1983), estimate that the diameter of the duct of the sweat gland is approximately 40 microns. According to Scheupoein and Blank, *Physiological Review*, 51(4): 702–747 (1971), the average density of sweat glands on the skin surface is approximately 250 per square centimeter. Thus, the total surface area of sweat gland ducts of the skin represent 1/318 of the total surface area of the patch of the instant invention. The visible result on a test patch of the present invention when, for example, using known ELISA technology to determine a low concentration analyte, is the appearance of a number of tiny color changes on the binder or absorptive layer associated with the output of specific ducts. If significant lateral diffusion of sweat is permitted prior to contact with the immobilized binding partner, the color change is frequently too diffuse to detect with the naked eye.

Although the etiology of perspiration is relatively complex, it is known to be caused by both mental states such as mental exercise and emotional stress; thermal stress, as the sedentary body's response to temperature control; and exercise stress as the physically active body's response to temperature control.

In addition to the foregoing distinctions, perspiration can be either insensible or sensible. Insensible sweat appears to be caused by water diffusion through dermal and epidermal layers. Its purpose appears to be not related to thermal regulation at all, but to aid in such things as the improvement of mechanical interaction between the skin and surfaces to facilitate grip. Further complexities arise with regard to the spatial distribution of sweat glands and the flow rates of the various types of perspiration. Specialized areas of the palms and soles of the feet sweat continuously, although at a very low rate. The rate of insensible perspiration is dependent upon the position of the particular area in question relative to the heart. For example, elevating a limb over the heart decreases the insensible perspiration rate in that limb.

At temperatures of about 31° C. in a resting human adult, insensible perspiration proceeds at a rate of between about 6–10 grams per square meter per hour from the skin of the arm, leg and trunk, up to about 100 grams per square meter per hour for palmer, planter and facial skin. The latter three areas jointly account for approximately 42% of the total water loss from the body due to insensible perspiration. Such insensible perspiration first begins on the dorsal surfaces of the foot and spreads to higher places on the body as the temperature increases. One reported study determined that the average water loss due to insensible perspiration for a body surface area of 1.75 square meters ranged from 381 ml, 526 ml and 695 ml per day at ambient temperatures of 22° C., 27° C. and 30° C., respectively.

In contrast to insensible perspiration which does not appear to be associated with a particular surface element of the skin, sensible perspiration has been associated with the eccrine gland. The number of actively secreting eccrine glands varies among individuals and depends upon the part of the body observed and the type of sweat response created. Maximum gland density varies from between about 200 per square centimeter on the forearm to over 400 per square centimeter on the thenar eminence.

The appearance of sensible sweat begins at either when the skin temperature exceeds about 94° F. or the rectal temperature exceeds about 0.2° F. over normal core temperature. Maximum rates of sweat volume loss can be as high as 2 liters per hour in average subjects and can be as high as 4 liters per hour for brief periods. Sensible perspiration begins in the distal parts of the lower extremities and progresses upward as the environmental temperature is elevated. Thus, the dorsum of the foot begins to sweat long before the chest. The pattern of sensible sweat response also shifts from one region of the body to another as the thermal stress increases. Under mild thermal stress, sweating is present mainly in the lower extremities. As the thermal stress further increases, sweating spreads to the trunk. Due to its large surface area, the trunk becomes the dominant water loss surface. Eventually, extremely high rates are found in the trunk while rates in the lower extremities may actually decline. The forehead can produce extremely high sweat rates but is among the last areas to sweat in response to thermal stress.

B. Placement of Derreal Patches

Although a patch of the present invention can be worn at any practical location on the body, preferable locations for the patch include the skin on the sole of the foot and areas on the chest, back, and biceps. The patch is able to be worn in confidence in these areas, and these areas are not covered with excessive hair, so that the patch may be secured with conventional adhesive tapes.

The patch can advantageously be located on different regions of the body depending upon a variety of factors. It is well known that the quantity of perspiration generated is a function of both the location on the body, as well as the physical activity during and immediately preceding collection. This is due to both different densities of sweat glands on different regions of the body, as well as to certain regulatory functions of those glands.

Other desirable placement locations for the patches of the present invention will depend on the conditions under which it is desired to detect analytes. Using the parameters described above and other known factors, one of skill in the art will understand how to choose a desirable location on the body of a subject on which to place a patch.

III. Chemical Species Detectible with a Derreal Patch

A large variety of chemical species which are detectable in blood are also present in sweat, although typically in a much lesser concentration. Early investigation into the composition of perspiration centered on electrolytes, including sodium, chloride, calcium and potassium. Extreme individual variation was found among individuals, and the electrolyte composition also differed depending upon whether the sweat was stimulated by thermal, mental or other etiology.

Further research has identified numerous additional components in sweat, including both electrolytes and more complex biological molecules. Some illustrative chemical species which have been identified in sweat are identified in Table I below:

TABLE I

Chemical Components of Sweat

| | |
|---|---|
| diphtheria antitoxin | sulfates |
| ascorbic acid | iodine |
| thiamine | iron |
| riboflavin | fluorine |
| nicotinic acid | bromine |
| amino acids | bismuth |
| ethanol | lactic acid |
| antipyrine | pyruvate glucose |
| creatinine | nitrogen |
| C-14 methylurea | ammonia |
| C-14 acetamide | uric acid |
| C-14 urea | nicotine |
| thiourea | morphine |
| paraaminohippuric acid | sulfanilamide |
| mannitol sucrose | atabrin |
| lactate | methadone |
| sodium chloride | phencyclidine |
| potassium | aminopyrine |
| calcium | sulfaguanidine |
| magnesium | sulfadiacine |
| phosphorous | amphetamines |
| manganese | benzoylecgonine |
| theophylline | phenobarbital |
| parathion | androgen steroids |
| tetrahydrocannabinol | phencyclidine |
| insulin | phenytoin |
| cimetidine | carbamazepine |
| dimethylacetamide | |

Any of the entries in Table I for which affinity chemistry can be developed can be an appropriate subject of a test patch according to the present invention. Since most of the components listed in Table I are non-volatile, they will be trapped in the concentration zone 14 of the patch 10 illustrated in FIG. 1a, or on the binder layer 30 of FIG. 6. However, some components, most notably ethanol, would volatilize under the influence of body heat, thereby enabling escape in the vapor phase through the test patch. Where the analyte to be determined is ethanol or another volatile component, a patch of the present invention may be modified as described in connection with the embodiment illustrated in FIG. 2 to contain specific binding partners for the analyte.

In one preferred embodiment, the analyte to be determined in perspiration is the enzyme creatine kinase MB (CK-MB) which is expressed from the cardiac muscle during myocardial infarction and other cardiac distress. A monoclonal antibody raised against CK-MB can be immobilized to the microbeads in accordance with any of a variety of conventional methods, such as the cyanogen bromide technique described in Pharmacia product literature (Pharmacia, Inc., Piscataway, N.J.).

The antibody which is to be used for the purpose of complexing with CK-MB may be immobilized on any of a variety of supports known in the art. For example, anti-CK-MB antibody may be bound to polysaccharide polymers using the process described in U.S. Pat. No. 3,645,852. Alternatively, the antibody may be bound to supports comprising filter paper, or plastic beads made from polyethylene, polystyrene, polypropylene or other suitable material as desired. Preferably, the support will take the form of a multiplicity of microbeads which can conveniently be formed into microbead layer 32, illustrated in FIG. 3a.

Figure 1A:
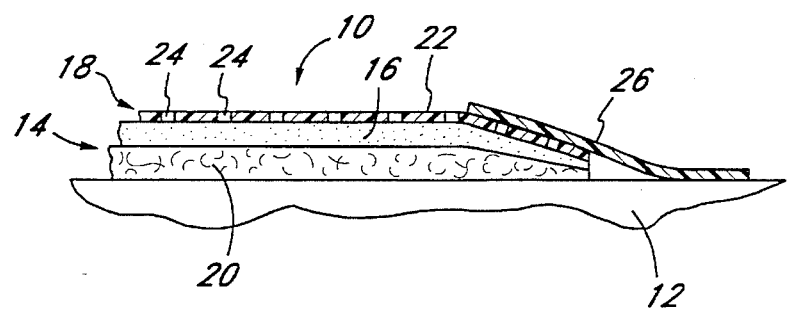

As an alternative to a microbead support layer, the specific binding partner could be immobilized directly to the inner porous layer 20 or 28 on FIG. 3a, to the underside of filter 16 of FIG. 1a, or to appropriate absorbent materials used in any of the embodiments of the dermal patch. In this manner, the need for microbead layer 32 could be eliminated entirely. Fluid permeable membranes which are specifically designed for binding antibody proteins are commercially available, such as Zetapor from Cuno, and Protrans, available from ICN in Costa Mesa, Calif.

The monoclonal antibodies useful in the present invention can be produced and isolated by processes which are well known in the art, such as those discussed by Milsrein and Kohler, reported in *Nature*, 256:495–497 (1975). In particular, Jackson describes a method of producing anti-CK-MM (an indicator of the status of skeletal muscles) and anti-CK-MB antibodies in *Clin. Chem.*, 30/7:1157–1162 (1984)).

Alternatively, the components of a commercially available diagnostic kit can be utilized which incorporate the CK-MM enzyme chemically bound to a bead support. A suitable kit marketed as the Isomune-Ck Diagnostic Kit by Roche of Nutley, N.J., is one commercially available candidate. This kit includes a goat antisera to human CK-MM and donkey anti-goat antibody covalently bound to styrene beads. A mixture would produce an immobilized conjugate having a specific affinity for human CK-MM. A more direct and less expensive procedure, however, would be to immobilize the anti-CK-MM monoclonal antibody directly to the microbead support in accordance with methods now well known in the art.

IV. Detecting Analytes

A. Using Color Change Chemistry to Detect Analytes

Figure 4:
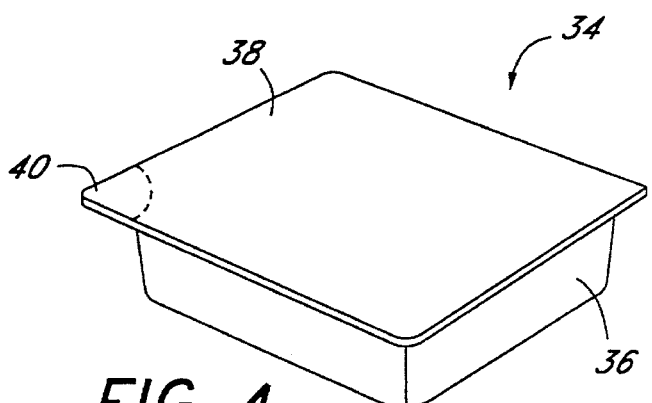
FIG. 4 is a perspective view of one embodiment of a reagent packet for use in effecting a color change responsive to the presence of analyte in the patch of the present invention.

Any of a number of methods known to the art can be used to detect an analyte collected on a patch of the present invention. One such method involves the use of color change chemistry to visualize the presence of an analyte on a patch. In this embodiment, after the test patch has been worn for a suitable period of time, it can be removed by the wearer (in non-drug screen tests) and developed to produce a visible indicium of the test result. Such a test patch can be marketed together with a developer packet such as packet 34 shown in FIG. 4 which contains known developer reagents for the immunoassay. The reagent packet 34 comprises a container 36 having a removably secured top 38. A flap 40 on the top 38 of the reagent packet facilitates gripping the top 38 and peeling away from container 36 to reveal the reagent contained therein. As an example, a protein electrophoresis stain such as Coomassie brilliant blue or amido black 10b, can be bound to purified analyte contained in the reagent packet 34. When a test patch is immersed in the packet 34, any antibodies on the test patch that are unbound by analyte in the perspiration will become occupied by stained purified analyte in the packet 34. There will thus be an inverse relationship between the amount of stain absorbed by the patch and the amount of enzyme passed through the patch. In this embodiment, the user would place the patch in the fluid of the packet 34, wait for some period of time such as 30 seconds or more, rinse the patch under tap water and relate the resultant color of the patch to the presence of the enzyme. A color comparison chart and control zone on the patch having no bound antibody may be provided to aid in this interpretation.

Alternatively, the user could support the test patch on an open vessel, such as a small jar or vial, or empty container similar in design to reagent packet 34 securing the adhesive border of the patch to the rim of the vessel, and then pour contents of packet 34 on top of the test patch. Gravity would assist the transport of the contents of packet 34 through the test patch to maximize the efficiency of the stain/binding reaction, and to facilitate visualization of the color change.

The system could readily be designed so that the user performs the interpretation of the concentration of the analyte not in the patch at all but by observing the packet contents once the contents have traversed the patch. This method would be similar to conventional ELISA assay methods where the packet contents contain enzyme conjugates which will react to specific enzyme substrates. The enzyme substrates would be added to the packet contents after those contents transversed the test patch.

If the perspiration contained molecules of interest, they would bind to the specific immobilized binding partner on the patch. If this occurred, enzyme conjugates in the packet would pass freely across the test patch and enzymatically modify the enzyme substrate producing a controlled color change in the solution in the packet. If the perspiration contained the desired molecules of interest, enzyme conjugates would then be bound in transit across the patch and would be unavailable to cause color change in the substrate solution. Other immunoassay schemes can be readily adapted for use in the present invention by one of skill in the art.

A variety of well known immunoassay schemes for visualizing the presence of an analyte of interest are well known in the art, and need not be detailed here. However, the optimal immunoassay scheme is generally one which is simple and requires the fewest steps. For many types of assays, it will be desirable for the wearer to obtain rapid results such as a color change to demonstrate a positive or negative result with as few steps as possible. On the other hand, drug of abuse screens are more likely to be evaluated by clinical staff instead of by the test subject, and there is less concern for a "user friendly" product.

For example, in a patch of the present invention designed for determining both the presence of CK-MM and CK-MB enzyme, the immobilized specific binding partner for each of those enzymes will be segregated to separate regions of the test patch. In this manner, if an enzyme-linked immunoassay system is utilized, a common enzyme and a common substrate could be used. Alternatively, a different color can be used to express the presence of different analytes.

B. Detecting a Metabolite of an Analyte Collected on a Patch

One problem which has been encountered in detecting analytes contained in patches, especially when such analytes are drugs of abuse, is that many conventional systems for performing drug testing do not test for the analytes which are collected on a patch but rather for the metabolites of such analytes. This is because the analytes themselves are not expressed in some body fluids. For example, cocaine is present in perspiration but not in urine. Therefore, urine is not tested for the presence of the cocaine molecule itself but rather for the presence of the major urine metabolite of cocaine in man, benzoylecgonine ("BE"), in order to detect cocaine use by a subject.

Currently, the primary method for the diagnosis of drug abuse is by urine analysis. Many conventional diagnostic systems, therefore, are designed to screen for drug analytes (or their metabolites) in urine. For example, numerous companies have developed very sophisticated automated systems to quantify cocaine metabolites in urine. Such systems are highly sensitive to the presence of the major cocaine metabolite in human urine, benzoylecgonine or BE. However, since the cocaine molecule itself is not present in urine, many of these systems, such as the SYVA EMIT system (Palo Alto, Calif.) and Roche RIA system (Nutley, N.J.), are virtually blind to the cocaine molecule itself.

In order to take advantage of conventional diagnostic systems that perform drug abuse testing by urinalysis, it is important that the drug contents of a patch of the present invention be measurable by such diagnostic systems. Unfortunately, most of the kits on the market which test for the presence of analytes such as cocaine are designed to detect metabolites of such molecules rather than the analytes themselves. In order to utilize such diagnostic systems to test for a desired analyte, therefore, the contents of a patch must be chemically modified.

In accordance with another aspect of the present invention, therefore, an analyte contained in a patch which is not detectable by conventional diagnostic systems, particularly systems for performing urinalysis, is chemically modified so that it can be detected by such systems. In this aspect, an analyte passed through the skin of a subject in perspiration is collected on an absorbent material in the patch. The analyte can then be chemically modified and detected while still in the absorbent layer or while bound to a microbead in a microbead layer. Alternatively, the analyte can be freed from the absorbent material, such as through chemical elution or by dissolving the absorbent material, in order to allow the analyte to be detected by a conventional diagnostic system. The analyte is then chemically modified so that it can be detected in such a diagnostic system.

As long as the analyte and the metabolite of that analyte which is detected by a diagnostic system are known and a means of converting the analyte into its metabolite is known, it is within the knowledge of one of skill in the art to chemically modify such an analyte so that it can be detected. Thus, any such analyte contained in a patch of the present invention can be tested using conventional diagnostic systems. However, an example of how to chemically modify a particular analyte commonly tested for, cocaine, will be detailed below.

Cocaine is metabolized in the body by either pH changes or cholinesterase enzymes. Cocaine is unstable at pH values higher than 7, and thus can be converted to BE either through exposure to high pH or to cholinesterase enzymes. Therefore, in order to chemically modify the cocaine on a patch and convert it to BE in order to make it detectable by conventional urinalysis, cocaine molecules can be extracted from the patch and then exposed to a solution at pH 11 at room temperature for 10 minutes or more. Following this modification step, the patch extract is returned to a neutral pH and then analyzed with conventional diagnostic systems. As is obvious to one of skill in the art, other methods of hydrolyzing the ester linkages of the cocaine molecule in order to produce BE, such as through the use of enzymes, can also be performed in order to prepare an extract of a patch of the present invention so that it can be detected by conventional diagnostic systems.

C. Eluting Analytes from Dermal Patches

Another difficulty encountered in detecting analytes that are contained in perspiration and collected on a patch is that, unless color change chemistry is used to detect such analytes, these analytes usually have to be removed from the patch in order to detect them. Removing the analytes normally involves chemically eluting them from the patch, which is both labor intensive and time consuming.

Therefore, in yet another aspect of the present invention, a patch is provided in which the absorbent material of the patch on which analytes are collected is dissolvable. When such absorbent material is dissolved, the analytes contained therein are made available for detection through further diagnostic procedures. As in other embodiments of a patch of the present invention, a patch incorporating a dissolvable absorbent material is placed in fluid communication with the skin of a subject in order to collect analytes contained in perspiration. Such a patch also preferably contains a gas permeable layer between the absorbent material and the outside of the patch in order to allow the fluids expressed through the skin in perspiration to escape to the outside of the patch in their vapor phase.

The analytes of interest that are collected on the absorbent material are preferably able to withstand the chemical treatment which results in the dissolution of the absorbent material. Thus, the dissolution of the absorbent material will not affect the analysis of the analytes contained in the absorbent material. One of skill in the art will be able to recognize whether a particular analyte will be chemically changed by a particular chemical treatment used to dissolve the absorbent material. If one of skill in the art would be unsure as to whether a particular analyte would withstand such chemical treatment, it is a matter of routine experimentation to treat a sample of the analyte under the conditions of the chemical treatment and then determine whether the analyte has been chemically altered.

In another embodiment, the chemical treatment of the absorbent material converts an analyte of interest contained in the absorbent material into a detectable metabolite or into some other detectable species. For example, the treatment of cocaine with a strong base converts it into BE, a common cocaine metabolite found in urine. The same strong base can also be used to dissolve an absorption disk made from a material sensitive to strong bases. In this embodiment, the dissolving of the absorbent material does not interfere with the analysis of the analyte contained in the absorbent material, but instead actually allows the analyte to be analyzed.

An absorbent material for use in this aspect of the present invention can be made from any of a variety of materials which can be chemically dissolved. For example, a number of materials are variously susceptible to chemical attack and dissolution by acids and/or bases. Among these materials are Nylon 6/6 (sold as Vydyne 909 by Monsanto Co., St. Louis, Mo.), Phenolic (sold as Polychem 102 by Budd Co.), Polyester (PBT) (sold as Celanex 3300-2 by Celanese Plastics), and polyurethane (TP) (sold as Pellethane 2363-55D by The Upjohn Co.). To dissolve any of these materials, an appropriately strong acid or base is added the material, as is known to those of skill in the art.

Absorbent materials can also comprise a woven protein web, such as a web made from protein fibers approximately 0.03 inches thick. Such fibers are disclosed by Baumgartner, *J. Forensic Sciences,* 34:1433–1453 (1989)).

Another dissolvable material which can be used as the absorbent material in the patch of the present invention is polystyrene. In this embodiment, solvents of lo polystyrene can be used to dissolve such absorbent material. Such solvents include chlorinated and aromatic hydrocarbons, esters, ketones, essential oils of high terpene content and turpentine. Specific examples of such solvents include cyclohexanone, dichloroethylene, and methylenedichloride.

Materials and solvents other than those listed above, of course, can also be used in this aspect of the present invention. The foregoing materials and solvents are therefore exemplary of this aspect of the present invention and not intended to be limiting.

V. Quantitative Determination of an Analyte in Perspiration

A. Derreal Patches for the Quantitative Determination of an Analyte

In another aspect of the present invention, the amount of an analyte that is present in a given volume of a subject's perspiration can be discovered. An embodiment of this aspect of the present invention is illustrated in FIG. 11. In this embodiment, a fluid permeable support layer 120 is in fluid communication with the skin 12 of a subject mammal, such as a human, and is located between the skin 12 of the subject and an absorptive layer 130 made of an absorptive material.

In the embodiment illustrated in FIG. 11, the support layer 120 also comprises a rate-limiting structure which limits the passage of perspiration from the skin 12 to the absorptive layer 130 to a rate lower than the rate of insensible perspiration of the subject. The insensible rate of perspiration is the rate of continuous perspiration of a subject which occurs without regard to the regulation of the temperature of the subject and which is not normally noticed by that subject. For humans, the rate of insensible perspiration of sweat glands in the arm, leg or trunk is approximately 6–10 ml/m*m*hr (Randall, W. C., *Am. J. Phys. Med.,*32:292 (1953)). Since the rate of perspiration of the subject will almost always be equal to or greater than the rate of passage of such perspiration through the rate-limited support layer 120, the rate of perspiration passing into the absorptive layer 130 can be kept approximately constant.

The rate-limited support layer 120 can be made from any material which can control the rate of diffusion of the components of perspiration. For example, diffusion can be controlled by a membrane. The rate of diffusion of any particular membrane is related to physical characteristics of the membrane such as its molecular composition, thickness, and, in the case of a porous type of membrane, its pore size. One example of a porous type of membrane which can be used as a rate-limited structure in this embodiment of the present invention is a polyester-supported polycarbonate microporous membrane, such as that manufactured by Nuclepore (Menlo Park, Calif.). The pore density, pore size and thickness of the membrane can be adjusted to provide the necessary limited fluid transport rate for this application. Another example of a porous membrane is nylon 6,6, such as that manufactured by Pall Corp. (Glencove, N.Y.).

An alternative to using a porous type rate-limited membrane is to use a ratelimiting structure comprising a dialysis or osmotic non-porous membrane. Such membranes have the advantage of having molecular weight specificity, which may increase analyte sensitivity. For example, if one were interested in collecting a therapeutic drug or its metabolites in the absorptive layer 130 and these analytes had a molecular weight of 1000 Dalton, one could choose a dialysis membrane which would pass only molecules which are smaller than 2000 Dalton in size. Larger molecules would be excluded from passing into the absorptive layer 130. By limiting the molecules which pass into the absorptive layer 130, interference by other components in perspiration in the laboratory analysis of the analyte in the absorptive layer 130 is minimized. Although the support layer 130 of this embodiment of the invention has been described as comprising a rate-limited structure, one of skill in the art will recognize that the support layer 130 and the rate-limited structure can be two separate membranes or structures in fluid communication with each other.

The absorptive layer 130 is located distally of the support layer 120 so that said support layer 120 is between the subject's skin 12 and the absorptive layer when the patch is being worn. The absorptive layer can be made from any number of absorbent materials. If passive absorption of an analyte is adequate to capture that analyte on the patch, then a layer of medical grade paper such as Filtration Sciences medical grade paper (FS#39) will suffice. If active absorption is required then substances such as monoclonal antibodies specifically tailored for high affinity to the analyte can be chemically coupled to the absorptive layer 130 in order to concentrate the analyte on the absorptive material, as previously described.

In this embodiment of the invention, a gas permeable layer 140, which in a preferred embodiment is also an outer protective layer, is located distally from the skin 12 of the subject on the side of the absorptive layer 130 opposite that which borders the support layer 120. The gas permeable, outer protective layer 140 can be made, for example, from 1625 Tegaderm wound dressing made by the 3M Company (St. Paul, Minn.). In a preferred embodiment, the gas permeable layer 140 extends beyond the areas of skin 12 covered by the support layer 120 and the absorptive layer 130 when the derreal patch 110 is applied to the skin 12 of a subject. In this way, the support layer 120 and absorptive layer 130 are protected from external abrasion and wear.

A means for attaching the patch to the skin of a subject is also preferably applied to a portion of the outer protective layer 140 which extends beyond the support layer 120 and the absorptive layer 130. Most commonly, the means for attaching is an adhesive composition. For example, in a patch 110 in which the outer protective layer 140 (excluding that portion to which an adhesive is applied) is approximately 14 cm$^2$, an adhesive can be applied to an area of approximately 1 cm around the outer perimeter of the outer protective layer 140 on the side of the outer protective layer 140 in contact with the subject's skin in order to attach the patch 110 to the skin 12 of a subject.

In a more preferred embodiment, a pooling area 150 is formed between the outer protective layer 140 and the subject's skin 12 when the patch is worn on the subject's skin 12. Such a pooling area 150 can be formed, for example, by an area 152 of the outer protective layer 140 which extends beyond the support layer 120 and the absorptive layer 130 and to which no adhesive is applied. Such a pooling area 150 collects the excess perspiration that is not diffused across the support layer 120 and allows it to dissipate into the environment across the outer protective layer 140. By providing such a pooling area, the back-diffusion of the components of perspiration across the skin 12 is minimized, since excess perspiration which is unable to pass into the absorptive layer 130 is shunted into the pooling area 150. Since the rate of flow of perspiration into the absorptive layer 130 is controlled by the rate-limiting structure of the support layer 120, the absorbent material of the absorptive layer 130 is in fluid communication with the pooling area 150 only through the support layer 120.

This pooling area is unattached to the subject's skin, and provides a sufficient amount of space to accommodate extra perspiration which does not pass across the rate-limited structure of the support layer 120. For example, during times of heavy exercise, the rate of perspiration of the subject might rise well beyond the rate at which perspiration can be passed into the absorptive layer 130. During such times of heavy perspiration, the pooling area 150 acts as a "shunt" to divert perspiration away from the support layer 120. The volatile components of such perspiration then evaporate through the gas permeable layer 140. In this way, the back-diffusion of perspiration and the buildup of bacteria under the rate-limited structure of the support layer 120 can be avoided or at least mitigated.

B. Using Derreal Patches to Determine the Amount of an Analyte in Perspiration

In order to determine the length of time a patch has been worn, the amount of a reference analyte contained in a certain volume of perspiration of a subject must first be determined. This analyte must be present in an approximately constant amount in a given volume of perspiration for the period of time that the patch is worn by a subject. Once such an analyte and its concentration in perspiration is known, the amount of time a patch is worn can be determined because the rate at which perspiration passes into the absorptive layer is held approximately constant by the rate-limited structure. Since the rate of passage of perspiration is known and the amount of the reference analyte in a given volume is known, once the total amount of the analyte in absorptive layer is known the amount of time the patch has been worn by a subject can be determined.

The volume of perspiration concentrated on a patch can also be determined through the use of this embodiment of the present invention. The rate-limited structure of the support layer 120 in this embodiment is preferably designed to allow the passage of perspiration to the absorptive layer 140 at a rate lower than the minimal rate of passage of perspiration through the skin, thereby assuring a relatively constant rate of flow of perspiration into the absorptive layer 140. The total volume of perspiration concentrated on the absorption disk is thus directly related to and can be determined by the duration of wear.

In order to quantitatively determine the amount of an analyte contained in a given volume of a subject's perspiration, a patch having a rate-limited structure as described above is first placed on the skin of a subject, preferably a mammal. Perspiration is then passed across this rate-limited structure at a known rate. For example, if the rate at which perspiration is allowed to pass across the rate-limited structure is equal to or less than the insensible rate of perspiration of the subject, perspiration will pass into the absorbent material at approximately a constant rate. After a sufficient test period of time has elapsed to allow a detectable amount of the analyte to be tested for to pass into the absorbent material, the patch is removed from the skin of the subject. When the patch is removed, the amount of time between the placement of the patch on the skin of the subject and the removal of the patch is recorded.

In order to then determine the total volume of perspiration which has passed into the absorptive layer 140 and concentrated analytes there, the rate of flow of perspiration into the absorptive layer 140 (as determined by the rate at which perspiration passes across the rate-limited structure of the support layer 120) is first multiplied by the amount of time the patch has been worn. This figure indicates the volume of perspiration which has passed through the support layer 120 and into the absorptive layer 130. The total quantity of analyte in the absorptive layer is then determined. By dividing the total amount of analyte present by the total volume of perspiration which has passed into the absorptive layer 130, the average amount of the analyte in a given volume of the subject's perspiration can be determined.

The above described aspect of the present invention is thereby suited to be used in many areas of diagnostics where quantitative information about a particular analyte is necessary. For example, this invention can be used to monitor therapeutic drug administration, determine the nutritional adequacy of a subject's diet, or explore hormonal imbalances in a particular subject.

VI. Increasing Analyte Concentration and Controlling Back-Diffusion in a Dermal Patch

A. The Problem of Back-Diffusion

An analyte which has passed through the skin in perspiration is usually removed from the exterior surface of the skin through washing or through various natural processes. Thus, such an analyte will not normally accumulate on the skin's surface. However, analytes which pass into a derreal patch can become more highly concentrated than they normally would on the surface of the skin. If an analyte does become concentrated on a derreal patch, it becomes possible for that analyte to diffuse back through the skin of the subject wearing the patch, a phenomenon which has been termed "back-diffusion".

Previous reports in the literature suggest that an analyte will back-diffuse after the concentration of the analyte on a derreal patch rises above the concentration of the analyte in the sweat or interstitial fluid of a subject. In fact, a mathematical model has even been generated to elucidate the pharmacokinetics of back-diffusion (Peck, Carl C., et al., "Continuous Transepidermal Drug Collection: Basis for Use in Assessing Drug Intake and Pharmacokinetics", *J. Pharmacokinetics and Biopharmacology*, 9:41–58 (1981)). This model suggests that back-diffusion will occur when an analyte is concentrated on a derreal patch, and that such back-diffusion must be prevented in order to accurately quantitate the amount of an analyte which passes into a derreal patch. Thus, many prior art references suggest using specific binding chemistry to prevent back-diffusion.

B. Back-Diffusion and Dermal Patches of the Present Invention

It is one of the surprising discoveries of the present invention, however, that such specific binding chemistry is not necessary to prevent back-diffusion. This discovery was first made during the experiment illustrated in FIG. 12, in which a patch without any specific binding chemistry was placed on the skin of a subject who had ingested cocaine. In this test, the concentrations of cocaine and cocaine metabolites found on the patch were charted for approximately 200 hours following the subject's ingestion of cocaine. The results of this test showed that the concentration of cocaine on the derreal patch rose immediately during the first hours of the test, and thereafter stayed at approximately the same level for the remaining 200 hours. Thus, the patch was able to concentrate analytes over a period of almost 200 hours without exhibiting significant back-diffusion.

Figure 12:
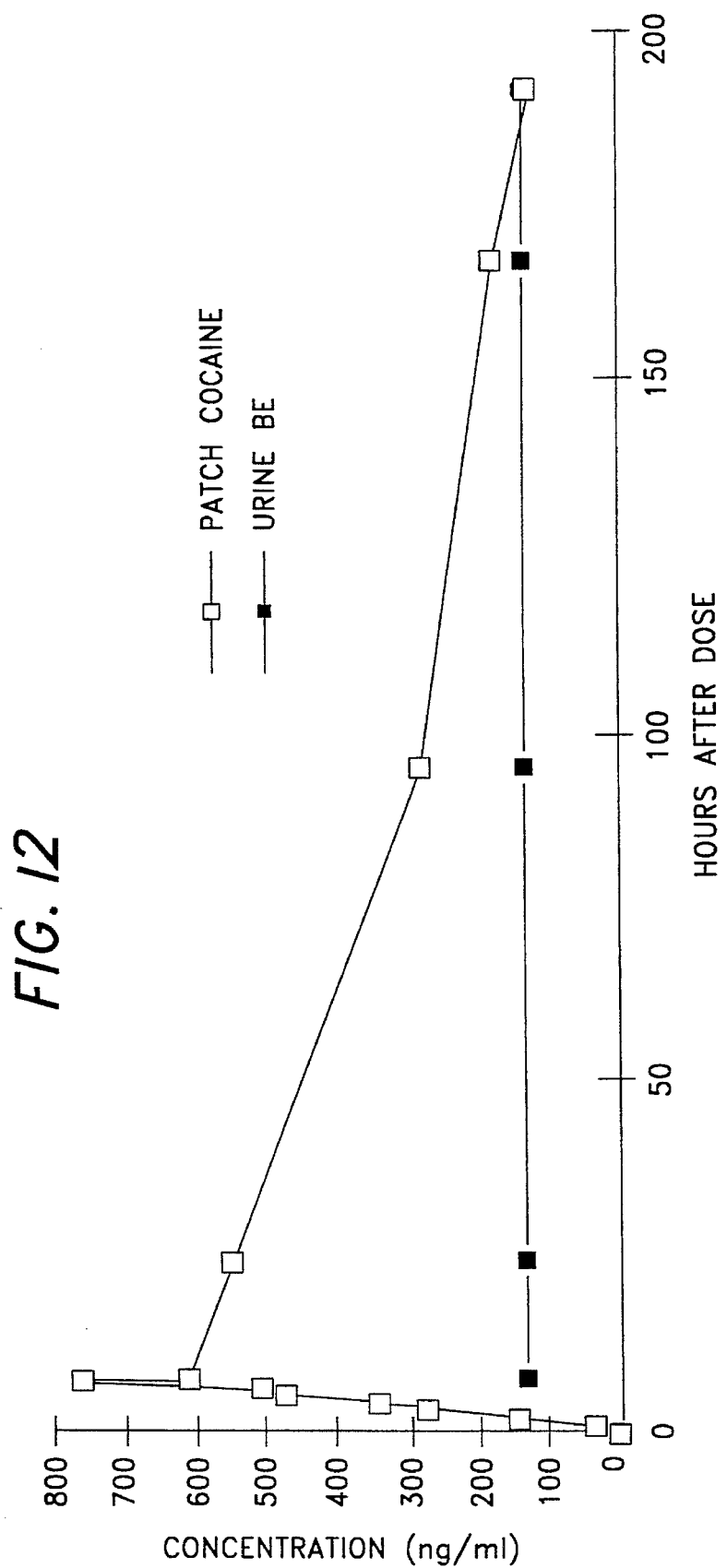
FIG. 12 is a chart illustrating the results of a test of a derreal patch of the present invention. This chart compares the amount of cocaine collected on a patch placed on a subject who ingested cocaine versus the amount of BE detected in the urine of that subject over the course of almost 200 hours.

Furthermore, during that 200-hour time period, the concentration of cocaine in the subject's system was decreasing, as shown in FIG. 12 by the declining concentration of BE in the subject's urine. Thus, the derreal patch used in this test was able to maintain a concentration of cocaine that was higher than that in the subject's system, again demonstrating that significant back-diffusion was prevented. These results were unexpected in light of the teachings of the prior art, which would have led one of skill in the art to expect to observe back-diffusion during this test.

It is believed that the surprising results of this test were due to the ionization states of the analyte of interest collected on the patch, in this case cocaine. In the experiment illustrated in FIG. 12, the ionization states of the cocaine molecules collected on the dermal patch used in that experiment were affected by the pH of the derreal patch and the pH of the exterior surface of the skin underneath the patch relative to the pH of the body fluids beneath the surface of the skin, as well as by the $pK_a$ of cocaine. It is the interaction of these pH and $pK_a$ values which affects the ionization state of an analyte.

The occurrence of back-diffusion can be substantially prevented by controlling the ionization state of an analyte being collected on a dermal patch. For example, the pH of a derreal patch can be controlled in order to also control the pH of the surface of the skin beneath that patch. Once analytes pass through the area of skin underneath such a dermal patch having a controlled pH, they will become ionized and thus substantially unable to back-diffuse. Thus, after determining the $pK_a$ of an analyte of interest, standard pharmacokinetic equations can be used to determine pH values at which that analyte will become ionized once it passes to the surface of the skin of a subject. In this way, a particular analyte of interest can be collected on a dermal patch without the risk of subsequent back-diffusion.

We believe that one reason that the ionized form of various analytes do not back-diffuse is that these ionized analyzed can attach themselves to larger molecules that are too large to be capable of back-diffusion.

C. The Effect of Occlusion on Back-Diffusion

In order to evaluate this model for controlling back-diffusion, the pH of skin underneath a non-occlusive patch such as that used in the experiment illustrated in FIG. 12 was next determined by conducting a further test. In this test, patches were constructed which had ½" long pieces of litmus paper between the absorptive layers and the Tegaderm outer layers of each of the patches, and which further had ½" long pieces of litmus paper between the skin and the absorptive layers of these patches. Such patches were placed on the chests (below the diaphragm) and biceps of each of three male volunteers for seven days. The colors of the pieces of litmus paper in each patch were monitored while these patches were worn.

The results of this experiment indicated that in all three volunteers the pH of both the volunteers' skin and the absorptive layers of each of the patches reached only between about 4.5 and 5.0. Further, this pH was reached and thereafter maintained in each case within 24 hours. Human skin normally has a pH of about 4.4. Thus, the application of a non-occlusive patch does not appear to significantly change the skin's pH.

By comparison, occlusion of the skin can bring about a much greater change in the skin's pH. In a study done on the effects of occluding skin, the skin of ten subjects was wrapped with plastic film (Saran brand plastic wrap) for approximately five days. The results of this test showed that the pH of the skin of these subjects shifted gradually over the course of the test from 4.38 before occlusion to 7.05 on the fourth day of occlusion (Aly, Raza, et al., "Effect of Prolonged Occlusion on the Microbial Flora, pH, Carbondioxide and Trans-Epidermal Water Loss on Human Skin,"

*Journal of Investigative Dermatology,* 71:378–381 (1978)).

As discussed in further detail below, a rise in pH values such as that observed in the occlusion tests performed by Aly can significantly affect the amount of backdiffusion from a dermal patch. Prior art patches, which are occlusive in nature, appear to have experienced problems with backdiffusion due to an unintended and undiscovered shift in the pH of the skin below such patches. By contrast, the nonocclusive nature of the derreal patches of the present invention results in only a small change in the pH of the sudace of the skin under such patches. Since the skin is naturally slightly acidic, the maintenance of a relatively acid pH will prevent backdiffusion problems. The detrimental effects of a rise in pH on analyte absorption can thus be obviated by using the patches of the present invention.

D. Controlling Back-Diffusion

The transport of many substances across the skin, including the back-diffusion of analytes, is believed to occur by means of passive diffusion across the stratum cornium, a structure which has a high lipid content (Orland, 1992). Passive diffusion across a lipid barrier normally occurs only if the substance in question is non-ionized, because ionized molecules cannot cross such a barrier (Labaune, J. P., "Handbook of Pharmacokinetics," 1989, pp. 18–25). In order to control back-diffusion, therefore, the pH of the surface of the skin below a derreal patch can be controlled, such as with a buffer, so that analytes which pass through the stratum cornlure become ionized once they reach the surface of the skin, thereby losing their ability to pass back through the stratum cornium.

Alternatively, back-diffusion can be prevented by ionization of analytes in other ways known to those having ordinary skill in the art. For example, analytes can be ionized by electricity, such as by iontophoresis. Devices such as the Phoresor II$^{TM}$ (made by Iomed, Inc., Salt Lake City, Utah) can be outfitted to ionize analytes collected on patches. These devices, which were originally designed to deliver drugs by means of electrodes attached to the skin, can be adapted to deliver electricity to a patch or to the skin adjacent the patch. However, other methods can be used to deliver electricity to the patch or skin, such as by simply attaching a pair of electrodes connected to a battery or other source of electricity.

It is believed that an analyte which has passed into a patch can also be bound onto a patch with an antibody and simultaneously ionized by means of an ionized molecule that is also bound to the antibody.

The degree of ionization of a molecule is easily determined if its $pK_a$ and the pH of its environment is known. The general Henderson-Hasselbach equation for a weak base shows:

$$pH = pK_a + \log(C_{nonion}/C_{ion})$$

Where:

$C_{ion}$ is the concentration of the ionized molecule; and $C_{nonion}$ is the concentration of the non-ionized molecule.

The concentration of an ionized molecule on either side of a lipid barrier, such as the skin barrier, can be found by extending the above equation for a weak acid molecule:

$$\frac{CB}{CP} = \frac{1 + 10^{(pHB-pKa)}}{1 + 10^{(pHP-pKa)}}$$

or for a weak base:

$$\frac{CB}{CP} = \frac{1 + 10^{(pKa-pHB)}}{1 + 10^{(pKa-pHP)}}$$

Where:

CB is the total concentration of the molecule in the interstitial fluid of a subject;

CP is the total concentration of the molecule in the patch;

pHB is the pH of the interstitial fluid;

pHP is the pH of the patch;

By using these pharmacokinetic equations, for any given analyte and subject, a pH can be selected for a patch which will cause the number of molecules of an analyte in the patch to be larger than the number of molecules of that analyte present in the interstitial fluid of the subject wearing the patch. When using a patch with such a selected pH, non-ionized molecules which pass through the stratum cornlure will tend to be ionized when they reach the patch, thereby preventing the back-diffusion of those molecules.

In practice, when collecting an analyte of interest on a dermal patch according to one preferred method of the present invention, a pH value or a range of pH values is first selected according to the equations above. The absorbent material of the patch is then preferably maintained at the selected pH or range of pH values in order to concentrate the analyte on the patch. As the patch is worn, the non-ionized form of the analyte in the interstitial fluid of a subject will naturally diffuse across the stratum cornium of a subject's skin in order to try and reach equilibrium with the non-ionized form of the analyte on the sudace of the subject's skin. Once on the exterior surface of the skin, the non-ionized analyte molecule will be ionized due to the selected pH of the patch, thus preventing the analyte molecule from back-diffusing. In addition, after the non-ionized molecule becomes ionized, the concentration of non-ionized analyte molecules on the surface of the skin will be decreased and thereby cause more nonionized analyte molecules on the interior side of the skin barrier to cross to the exterior side in order to try to reestablish an equilibrium concentration of non-ionized analyte molecules on each side of the skin barrier.

As discussed above, in prior art occlusive patches, the pH of the patch quickly approaches 7.05. This severely limits the ratio of analyte in the patch to analyte in the interstitial fluid. It is preferable, when using both occlusive and non-occlusive patches of this embodiment of the invention, to provide a ratio of analyte in the patch to analyte in the interstitial fluid of over 10, more preferably over 100. In one preferred embodiment, as illustrated below, such ratios can be provided by maintaining the pH of the patch below a given level.

An example of this method of collecting analytes on a dermal patch using a selected pH is outlined below. When using a non-occlusive patch, such as is described herein, the pH of the surface of the skin of a subject will remain at about 5.0. Perspiration as well as plasma and interstitial fluid all have a pH of about 7.2 (Orland, 1992). Using the equations above, it can be determined that when detecting the analyte cocaine, which is a weak base and has a $pK_a$ of about 8.7, the selected pH of 5.0 for the patch will drive the ratio of cocaine molecules on the exterior surface of the skin to that in the interstitial fluid to over 100. The number of ionized cocaine molecules on the exterior surface of the subject's skin compared to the number of non-ionized molecules is also much higher. Thus:

$$\frac{CB}{CP} = \frac{1+10^{(8.7-7.2)}}{1+10^{(8.7-5.0)}} = \frac{1+10^{1.5}}{1+10^{3.7}} \quad (1)$$

$$\frac{CB}{CP} = \frac{1+31.6}{1+5012} = \frac{32.6}{5013} = 0.0065 \quad (2)$$

$$CP = CB \times 154 \quad (3)$$

Applying the foregoing equations to prior art patches, in which the pH would quickly approach 7.05, the result would be CP=CB×1.4. Thus, by maintaining a patch pH of 5.0, a 110-fold increase in the ratio of concentration of analyte in the patch to concentration of analyte in the interstitial fluid can be obtained.

It can be seen that for weak base analytes such as cocaine, the higher skin pH observed under occlusive-type dermal patches will allow back-diffusion to occur. Thus, when it is advantageous to use an occlusive-type patch, such as when extra protection from the environment is desired, the pH of the skin under such an occlusive patch should be controlled in order to prevent back-diffusion. In these applications, a buffer can be used to control the pH of the surface of the skin below the patch. A buffer of any specified pH can be generated by controlling the ratio of acid to base in a mixture containing an acid and a base, such as a mixture of acetic acid and NaOH. Such a mixture can be made more basic by increasing the concentration of base, in this case NaOH, or can instead be made more acidic by increasing the concentration of acid. A buffer of this kind can maintain a desired pH in the patch and on the surface of the skin under the patch when the patch is worn. Thus, even if an occlusive dermal patch is used to collect an analyte, by controlling the pH of the patch the problem of backdiffusion can be virtually eliminated.

A particular application of the present invention is the prevention of the back-diffusion of a drug of abuse which has been collected on a dermal patch of the present invention. Table 2 below lists the $pK_a$'s of the major drugs of abuse, all of which are weak bases (Wilson, J., *Abused Drugs, a Laboratory Pocket Guide*, AACC Press, 1990).

TABLE 2

| Drug | $pK_a$ |
|---|---|
| Heroin | 7.6 |
| Methamphetamine | 9.9 |
| Amphetamine | 9.8 |
| Morphine | 8.1 |
| Phencyclidine | 8.5 |
| Cocaine | 8.7 |

The $pK_a$ for most of such analytes of interest is in the range of 7.2 to 10.0. The $pK_a$ values of an analyte of interest can be used in connection with the general Henderson-Hasselbach equation given above in order to determine the ratio of the ionized form of any given analyte to its non-ionized form in the patch. For analytes in this range of $pK_a$'s in prior art patches, in which the pH of the patch quickly approaches 7.05, the ratio of $C_{ion}$ to $C_{nonion}$ will vary from approximately 1.4 to approximately 891. As an example, for cocaine, which has a $pk_a$ of 8.7, this ratio will be 45 in a prior art occlusive patch. In contrast, using a patch of the present invention in which the pH of the patch is buffered to 5.0, the ratio will be 5012. In preferred embodiments of the present invention for both occlusive and nonocclusive patches, the ratio of ionized forms of the analyte to nonionized forms of the analyte in the patch will be over 1000, and more preferably over 5000.

As in the case of cocaine, using the equations described above it can be shown that a pH of about 5.0 on the surface of a subject's skin below a patch will cause the above-listed drugs of abuse to collect on the patch. Thus, for example, a non-occlusive patch of the present invention will concentrate the above analytes without the problem of back-diffusion.

In addition to solving the back-diffusion problems of prior art dermal patches, the present discovery also makes it possible to improve the ability of a dermal patch to concentrate an analyte. This can likewise be accomplished by adjusting the pH of a patch and the surface of the skin below the patch. By determining the $pK_a$ of an analyte of interest and using the equations above, an appropriate pH for the patch can be selected such that the equilibrium concentration of the ionized form of the analyte is much greater than the equilibrium concentration of the non-ionized form of the analyte. When non-ionized analytes then pass across the skin and into a patch having a pH selected in this way, they will be ionized, thus driving the further diffusion of non-ionized analyte molecules into the patch. Determining the $pK_a$ of an analyte of interest, if it is not already known, is within the knowledge of one of skill in the art, and thus requires only routine experimentation.

The present discovery further suggests a method of quantitatively determining the amount of an analyte which passes through the body of a subject. Such a method first involves the placement of a dermal patch on a subject. The back-diffusion of analyte molecules collected on this patch is controlled in this method, such as by selecting an appropriate buffer for the patch. After a specified period of time, the patch is removed from the subject's skin and the amount of time the patch was worn is recorded. The amount of an analyte which has passed into the patch is then determined. By preventing the back-diffusion of an analyte, the amount of analyte collected on the patch over the specified period of time will more closely reflect the amount of the analyte which passed through the subject's system over that period of time.

VII. Prevention of Tampering with Derreal Patches

In some uses of the present dermal patches, it is advantageous to provide a means for indicating whether a wearer has removed a patch during the examination period, particularly in situations where a wearer has an incentive to make sure that the patch produces a specific result. For example, if it is desired to determine whether a wearer has ingested a drug of abuse, safeguards are desirably provided to prevent tampering with the dermal patch.

A. Derreal Patches with Radial Slits

One embodiment of a patch for preventing tampering is illustrated in FIG. 8. In this embodiment, the patch 62 is secured to the skin 64 with an adhesive member 65. The adhesive member 65 is preferably constructed of a material that is strong enough to hold the patch 62 to the skin 64, but that is relatively easily torn such as during removal of the patch from the skin. A suitable material for use in this preferred embodiment is Tegaderm 1625, manufactured by Minnesota, Mining, and Manufacturing Corp. of St. Paul, Minn. Other companies, including Avery and Johnson & Johnson, manufacture similar suitable materials; the Johnson & Johnson product being sold under the trademark "Bioclusive." It has been found, however, that with sufficient patience, a wearer could remove an adhesive member of this type and replace it without leaving any visible indication that the adhesive member has been removed.

Therefore, in the particularly preferred embodiment shown, the adhesive member 65 has stress razors 66 in the form of a plurality of radial slits around its outer perimeter. The stress razors 66 can be arranged in any of a wide variety of configurations and densities and accrue the advantage of tearing upon removal, as will be apparent to one of skill in the art.

In the embodiment illustrated in FIG. 8, the radial slits 66 extend approximately 0.05 inches in length from the outer edge toward the center of the patch 62. The slits 66 may be arranged with any of a variety of regular or irregular spacings therebetween, and, in the preferred embodiment are preferably spaced approximately every 0.10 inches around the perimeter of the patch 62. The adhesive force of the material of the adhesive member 65 is preferably more than the force needed to tear the adhesive member at the stress razors 66, so that if the patch 62 is removed, the material of the adhesive member is torn. Thus, when a patch of this preferred embodiment is worn, a torn adhesive member serves as an indication that the wearer has likely tampered with the patch. Of course, the weakening of the adhesive member 65 may be accomplished by providing perforations rather than slits and the slits or perforations may be oriented in directions other than radially.

During storage prior to use, it is desirable to cover the adhesive member to prevent it from sticking to any surface; otherwise the stress razors 66 could become torn prior to use. Accordingly, in the preferred embodiment shown in FIG. 8, the patch is provided with an inner cover 69 to protect the adhesive member 65. The inner cover 69 is removed to expose the adhesive member 65 prior to application of the patch 62 to a subject's skin. Any of a variety of non-adherent materials known to those of skill in the art may be used for the inner cover 69, such as those commonly used to cover adhesive bandages.

The patch 62 is virtually impossible to remove and replace without showing visible signs of tampering. Thus, any analytes in sweat produced from skin under the concentration zone 14 during the time the patch is worn should be present in the patch.

However, a particularly shrewd subject desiring to produce false negative results could obtain additional test patches. This shrewd subject would obtain false negative results by removing the initially applied test patch and replacing the test patch just prior to the time the patch is to be removed for assay. In order to ensure that the patch removed from the subject is the same patch which was initially applied to the subject, an identifying marker which is difficult to reproduce can be incorporated into the patch. For example, a bar code identification strip 67, similar to the bar codes used at supermarket check out stands can be incorporated into the patch, preferably just below the adhesive member 65. For best results in protecting against replacement of the patch, it is important that the identifying marker not be easily removed and replaced without providing an indication that the patch has been tampered with.

In a preferred embodiment, the patch 62 has a filter 68 between the outer layer 65 and concentration zone 14, as described above in connection with FIGS. 1–3a. In a particularly preferred embodiment, the filter is a fluid permeable filter formed from a James River Paper Drape.

The preferred adhesive members of the embodiment shown in FIG. 8, made from adhesive materials, such as Tegaderm, which are relatively weak in strength, have generally been designed for hospital patients who are not expected to perspire at high rates. Therefore, the moisture vapor transmission rate (MVTR) of these materials is relatively low. For example, the MVTR of Tegaderm is approximately 810 g/m*m*day. However, an active person may perspire at instantaneous rates as high as 26000 g/m*m*day. Consequently, an active person may put out more sweat than these adhesive members can transmit to the atmosphere. If this sweat accumulates for any significant period of time, channels may be formed between the skin 64 and the adhesive member 65, allowing sweat to exit between the adhesive member and the skin, rather than be absorbed by the patch 62.

B. Derreal Patches with Pinhole Perforations

In accordance with a further embodiment of the present invention for preventing tampering, illustrated in FIG. 9, there is provided a patch 70 having an adhesive member 72 which allows excessive sweat to be freely transmitted to the outside through pinhole perforations 73. The pinhole perforations may be distributed throughout a wide band 75 extending from the outer perimeter of the adhesive member to a narrow band 77 surrounding the test region 821 of the patch 70.

Sweat produced beneath test region 81, over which there are no pinhole perforations 73, will be absorbed by the test region and will not be transmitted to the outside. The test region 81 includes the area of the patch 70 directly under the concentration zone 14 of the patch as well as the area immediately outside this zone. The narrow band 77 outside the concentration zone 14 of the patch has no pinhole perforations 73, and substantially restricts sweat forming underneath the test region 81 from communicating with the wide band 75 where sweat is transmitted to the outside.

The width of the narrow band 77, is preferably between 0.025 and 0.250 inches, more preferably between 0.05 and 0.125 inches. Narrow band widths less than the preferred width are not expected to keep contact with the skin, whereas narrow band widths greater than the preferred width may allow sweat channels to form, creating a path for sweat forming within the test region 81 to communicate with the outside.

C. Use of Soluble Markers to Prevent Tampering

A wearer of the patch in screenings for drugs of abuse would be expected to be rather creative in circumventing the protections of the patch. For example, a creative wearer could try to wash out the concentrated sweat components from the patch while the patch remains on the wearer's skin. Such washing could be attempted using a needle and syringe, such as those commonly used by intravenous drug abusers for drug injection. For those patches employing specific binding chemistry, attempted elution of the concentrated components using water would likely prove unsuccessful. Even for those patches not employing specific binding chemistry for the analyte being tested, elution with water alone would be difficult, requiring substantial volumes of water without triggering the detection of tampering through the removal of the patch from the skin. However, certain analytes could successfully be at least partially eluted using other solvents.

Thus, in order to detect tampering with the patch through elution of the patch's contents using water or other solvents, a known amount of a marker which is readily soluble in either aqueous or non-aqueous solvents, can be added to the concentration zone during manufacture of the patch. The marker should be easily quantifiable. The marker should also be soluble in either aqueous or non-aqueous solvents depending on the likely route of elution of the analyte. Additionally, the marker should be suitable for prolonged skin contact and not be readily absorbed by the skin. A variety of dyes used in the production of makeup have these suitable characteristics. Oil red N (catalogue number 29,849-2) sold by Aldrich Chemical Corp. of Milwaukee, Wis. is a suitable lipid soluble dye. DG01 red and DH60 yellow, both available from Virginia Dare Extract Co. of Brooklyn, N.Y. are suitable water soluble dyes. These water soluble dyes can be easily quantitated by elution from the patch followed by measuring optical density at 6500 nm for the red or 5800 nm for the yellow dye. The quantity of dye remaining can be compared with the range of the amount of dye found to be remaining in patches worn continuously without tampering for the same length of time.

Non-visible markers could also be used to prevent the wearer of the patch from obtaining feedback regarding the extent of marker remaining in the patch. A colorless protein could be used for this purpose. A protein should be chosen that is easily identified in the lab, and also not be expected in human sweat. For example, Bovine gamma globulins, such as those sold by Sigma Chemical Co. of St. Louis, Mo., could also be used as a marker. The presence of these markers can be easily ascertained using Bovine IgG RID kit, available from ICN of Costa Mesa, Calif.

Thus, when a suitable marker is employed within the patch, when the patch is analyzed for the particular analyte being tested, the patch can also be analyzed for the presence of the marker. For visible markers, such as makeup dyes, the presence of the marker may be analyzed by simply viewing the patch. For non-visible markers, the non-visible marker can be assayed along with the analyte. A significant decrease in the amount of marker present would be an indication of tampering through elution of the patch with a solvent.

D. Use of Adulterants to Prevent Tampering

A further method of tampering with the patch would be to add an adulterant to the patch which interferes with the assay chemistry. Numerous materials have been used to adulterate urine tests for drugs of abuse. The most commonly used, and generally most effective method of producing a false negative result in a urine test is to dilute the urine by ingestion of excessive amounts of fluids. Advantageously, this approach would not likely be successful in producing false negative results in the sweat collection patch of the present invention because interstitial concentration of drug metabolites is less likely to be influenced by ingestion of fluids.

However, the addition of certain adulterants to the patch may interfere with the analysis chemistry. For example, acids and bases are known to interfere with assays for many drug metabolites by altering the metabolites' molecular structure. Additionally, many household products, such as detergents, ammonia, ascorbic acid (Vitamin C), and drain openers have been used to interfere with urine assays. These products produce extremes of pH or changes in other chemical parameters, and would be expected to result in trauma to the skin if used in connection with tests using the patch of the present invention. This trauma could be noted by the technician removing the patch.

However, weak acids and bases, as well as eye drops sold under the trademark "Visine," are also known to interfere with a variety of assays for drug metabolites in urinalysis. However, these materials would not be expected to produce skin trauma. Thus, the use of these materials or other compounds interfering with an assay that do not cause skin trauma might go unnoticed by the technician removing the patch if the fluid contents of the material have had time to evaporate across the outer layer of the patch. However, "Visine" and most other adulterants would be expected to contain ionic materials.

Thus, in order to detect the use of an adulterant, test strips can be incorporated into the patch which will detect the presence of various ionic materials or of extremes of pH. Litmus paper, such as Hydrion pH test paper, available from Baxter Scientific Products, is well known as an indicator of variances of pH. Accordingly, a short piece, for example 1 cm by ½ cm, of litmus paper could be incorporated into the patch to detect the various household products identified above which are known to be highly acidic or basic.

Many test strips are also known for detecting the presence of ionic materials. For example Baxter Scientific Products supplies test strips from a variety of manufacturers for the detection of each of the following ions: aluminum, ammonium, chromate, cobalt, copper, ion, nickel, nitrate, peroxide, sulphite, tin, and calcium. In addition, test strips sold under the name "Qantab" are available from Baxter Scientific Products which identify the presence of chlorine ions. Other test strips available from the same supplier show glucose, protein, and ketones. Most of these test strips are read by simply comparing the color of the strips with a color chart included with the strips. Thus, the test strips provide a simple method of identifying the introduction of any of a variety of adulterant materials.

In order to detect adulterants, such as "Visine," which contain ionic materials not known to the person performing the test, the tester must first assay the adulterant using a variety of test strips for ions to ascertain which ions are present in the materials. Once the appropriate ions are detected, the test strips corresponding to those ions can be incorporated into the patch in order to provide an indication that the adulterant has been added to the patch.

Curiously, any particular adulterant might produce false negative results in some assays and false positive results in others. For each assay, the common adulterants which could be used to produce false negative results could be identified by testing the assays with the addition of small amounts of these known materials. Test strips could then be included which would detect the addition of these adulterants.

In a preferred embodiment, the test strip or strips are placed facing the skin, where the strips are not visible to the wearer. The wearer is thereby not provided any feedback which aids the wearer in deception.

E. Use of a Light Attenuation Layer to Prevent Tampering

Many biological compounds are known to be affected by various spectral bands of light energy. For example, urine samples for analysis of LSD must be kept from exposure to strong light. Schwartz, *Arch. Inter. Med.* 148:2407–12 (1988). Further examples of compounds which require protection from light include cocaine hydrochloride, *Martindale Extra Pharmacopoeia*, 29th Ed., p. 1213, and morphine sulphate, *Id.*, p. 1310. It is expected that these and other compounds may be affected by exposure to light while being concentrated in the collection patch as well.

Many analytes to be determined by a patch of the present invention may require collection and storage in the patch for prolonged periods of time (up to several weeks). These analytes are, therefore, exposed to substantial quantities of photoradiation. This quantity of photoradiation may be substantially greater than during a urine assay for the same or similar analyte. Also, many analytes have peculiarly high sensitivity to light. Thus, for analytes of peculiarly high photosensitivity or for those requiring prolonged collection and storage, it is particularly important to shield photosensitive analytes from light during prolonged storage in the patch.

Accordingly, in still another embodiment of the present invention, illustrated in FIG. 10, there is provided a test patch 90 having a light attenuation layer 92 between the outer adhesive layer 65 and the concentration zone 14. In FIG. 10, the adhesive layer 65, is shown having stress razors 66, however, this feature is to be understood as being optional in this embodiment of the invention.

The attenuation layer 92 is provided in order to attenuate the transmission of light into the concentration zone 14 where the biological compound of interest is being collected and stored. The layer 92 should be substantially impervious to the transmission of photoradiation, yet should also allow relatively unrestricted passage of the aqueous components of sweat to the outer adhesive layer 65. The layer 92 should be of sufficient porosity that diffusion of the aqueous components of sweat occurs at least as rapidly as sweat normally accumulates in the patch.

Because light of many wavelengths is capable of degrading the various biological compounds which may be of interest, the layer 92 should have optical properties which attenuate light throughout a wide spectrum. Attenuation can be achieved by either reflection or absorption of incoming light. Reflection may be achieved through, for example, the use of any of a variety of metallic surfaces. When used in accordance with certain preferred embodiments of the present invention, the attenuation layer 92 should allow passage of aqueous components of sweat. In order to provide a reflective layer with the suitable permeability, thin metallic foil with small holes can be provided. For example, aluminum foil, commercially available from many sources including Reynolds Aluminum Co., could be perforated with a plurality of small holes.

Absorptive attenuation layers can be provided through the use of a black surface. Preferably, these surfaces would continue to allow permeability of aqueous components of sweat. It is important that any dye or pigmentation in the attenuation layer 92 not bleed when exposed to the aqueous components of sweat and also that it not interfere with any binding chemistry or in the analysis of the analyte. Any of a variety of thin black papers having these properties are commercially available and are suitable for use as in the attenuation layer. For example, black Deltaware cellulose membrane filters available from Baxter Scientific Products have been found to be especially useful for use as an attenuation layer. This product is available in a variety of porosities; more open pores are preferred. Thus, in the preferred embodiment, 0.6 micron black Deltaware filters are provided.

In an alternative to the provision of an attenuation layer (not shown), the adhesive layer 65 can be made to attenuate light, either through absorption or reflection. As an example of an absorptive adhesive layer, black colorant, such as fine carbon black powder, could be incorporated into the extrusion of the adhesive sheet.

VIII. Accelerated Analyte Collection with Dermal Patches

In some applications of dermal patch technology, it is desireable to make long term, integral average diagnostic determinations of the concentration of an analyte in a subject's perspiration. For example, in order to monitor the compliance of subjects in a drug abuse program, analytes can be collected from the perspiration of such subjects with dermal patches which are worn for a period of days or weeks. The previously described dermal patches of the present invention are eminently suitable for such purposes.

In other applications, however, it is desirable to be able to determine the concentration of an analyte in a subject's perspiration in a much shorter period of time. For example, it can be desirable to be able to determine the concentration of a therapeutic drug in a subject's perspiration at a specific point in time. Also, when monitoring for substance abuse at the roadside (such as by a law enforcement officer) or on the job, it is beneficial to be able to obtain results within a very short period of time. This is particularly the case when the analyte to be detected is one which is rapidly processed by the body, such as alcohol.

It is one of the surprising discoveries of the present invention that a dermal patch can, in a relatively short period of time, collect enough perspiration to allow an analyte carried in such perspiration to be detected by conventional assays. While a dermal patch must normally be worn by a subject for at least 4 hours and perhaps for up to 24 hours before a diagnostically detectable amount of an analyte will collect in the patch, this period of time can be shortened to less than about two hours, and in a preferred embodiment to less than about 20 minutes, by applying heat to the area of skin where the patch is located.

A. Increasing the Rate of Perspiration Increases the Rate at which an Analyte can be Collected The discovery that a desired amount of an analyte can be collected in a short period of time was made during experiments designed to track the expression of the cocaine molecule in the perspiration of a subject. In the experiment illustrated in FIG. 13, a volunteer subject with recent cocaine experience who had given his informed consent to participate in the experiment was administered 32 mg of cocaine HCl intravenously. A derreal patch was then immediately placed on the subject's skin, and after 30 minutes this patch was removed and replaced by a new patch. Dermal patches were replaced at each of the time points shown on the horizontal axis of FIG. 13 so that the appearance of the cocaine molecule in the subject's perspiration and its concentration over various time periods could be determined.

Figure 13:
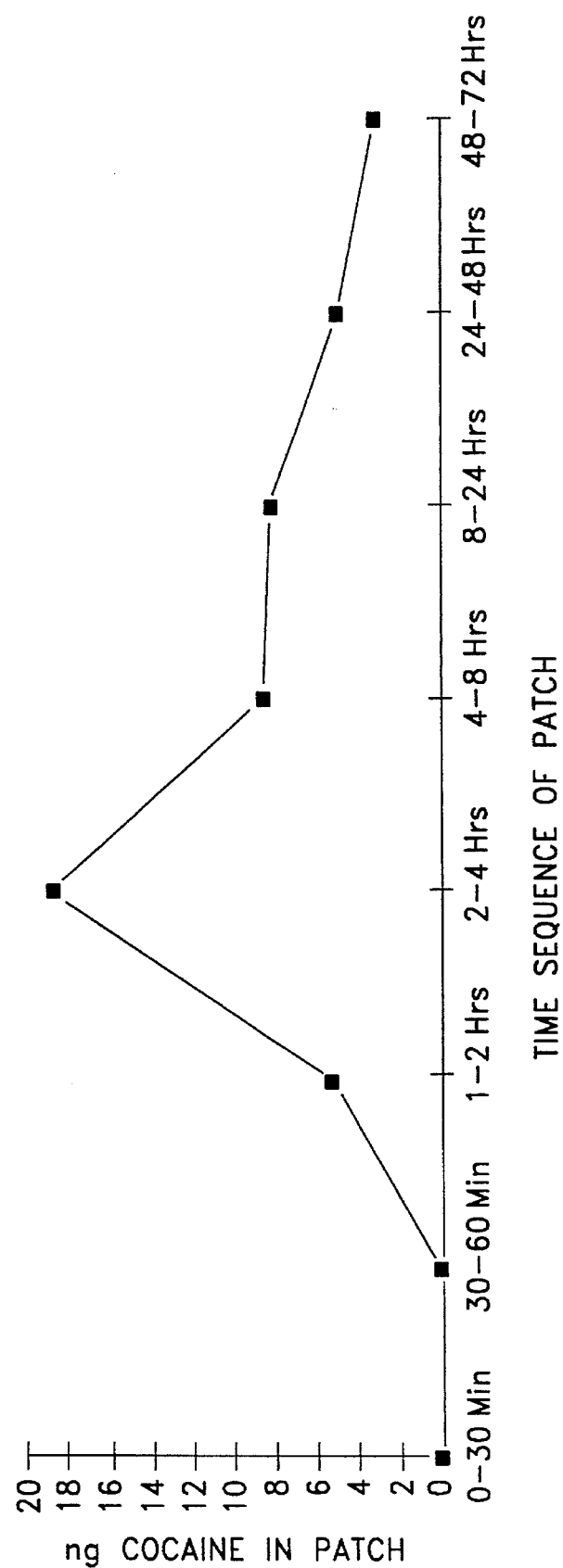
FIG. 13 is a graph showing the results of an experiment in which a derreal patch was placed on a subject who was administered 32 mg of cocaine intravenously. At the end of each of the time periods shown on the horizontal axis of the graph (representing the amounts of time following the administration of the cocaine), the patch worn by the subject during such period of time was removed and replaced by a new patch. The amount of cocaine found in each of these patches is charted on the vertical axis of the graph over the point on the horizontal axis corresponding to the period of time during which the patch was worn.

The amount of cocaine found in each patch is shown on the vertical axis of FIG. 13. The highest level of cocaine was found in the patch which was on the subject's skin from approximately 2 to 4 hours after the administration of cocaine to the subject. After the fourth hour post administration, a steady decline in the concentration of cocaine in the subject's perspiration occurred.

Figure 14:
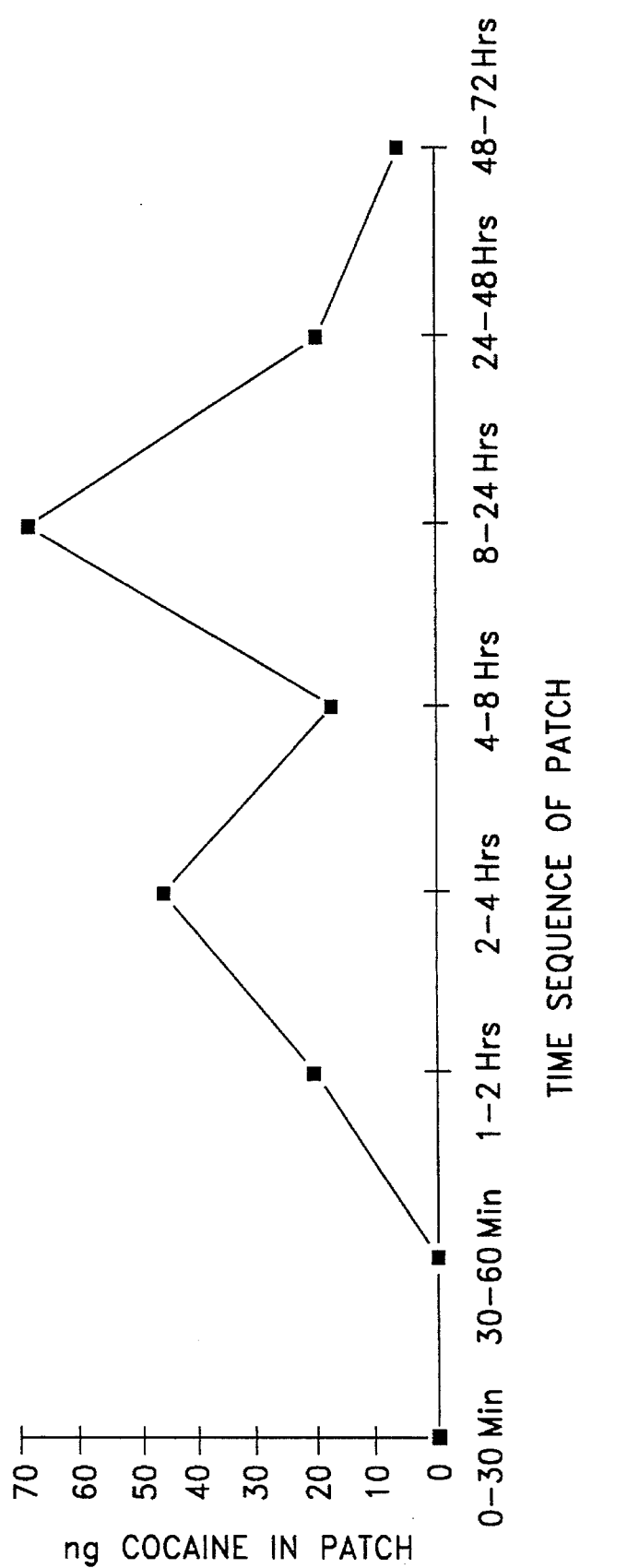
FIG. 14 is a graph similar to that of FIG. 13 showing another experiment involving the same subject. In this experiment, the subject was administered 42 mg of cocaine via smoking.

A similar experiment was later conducted on the same subject. In this experiment, 42 mg of cocaine was administered to the subject by having the subject smoke it. The results of this experiment are illustrated in FIG. 14 in the same manner as in FIG. 13. As in the experiment of FIG. 13, a peak in cocaine concentration occurs in the patch which was worn by the subject from 2 to 4 hours post administration, followed by a decline in the concentration of cocaine in the patch which was worn between 4 and 8 hours. The distinct feature of the experiment shown in FIG. 14 is the result from patch 5, which was worn from 8 to 24 hours after the administration of the cocaine. Rather than following the gradual decrease in cocaine concentration seen in the experiment of FIG. 13, there is a significant rise in concentration in the patch worn between 8 and 24 hours post administration in this experiment.

In order to determine the cause of the discrepancy between the results of the experiments of FIGS. 13 and 14, we investigated whether anything different had happened between 8 and 24 hours post administration in the experiment of FIG. 14 compared to the experiment of FIG. 13. It was discovered that the patch worn between 8 and 24 hours post administration in the experiment of FIG. 14 was wet with perspiration, unlike any of the other patches in either experiment. Apparently, the subject had actively perspired during the period that he wore this patch.

As a result of the subject's having actively perspired, significantly more analyte diffused into the patch worn between 8 and 24 hours post administration compared to the patch that was worn between 2 and 4 hours post administration. This was a surprising result because it appeared that any diminution which had occurred in the concentration of analyte in the subject's perspiration during active perspiration was compensated for by an increased rate of perspiration. This resulted in the collection of a proportionately larger quantity of analyte in the patch worn between 8 and 24 hours post administration in this experiment compared to the amount collected in the patch worn during the same period of time in the experiment of FIG. 13.

Active perspiration can be caused by an increase in the body's temperature, such as during exercise. A further experiment was therefore conducted to see whether an increase in the temperature of only one area of the body could cause localized active perspiration. In this experiment, a subject was administered 60 mg of codeine phosphate (in the form of Naldecon CX P.O., 30 ml), and a dermal patch was then placed on each of the subject's thighs. A heating pad which was heated to 105° F. was then placed over one thigh while the other thigh remained unheated. The patches were replaced each hour for six hours, and a final pair of patches was placed on the subject's thighs for one hour between 24 and 25 hours after the administration of the codeine.

Figure 16:
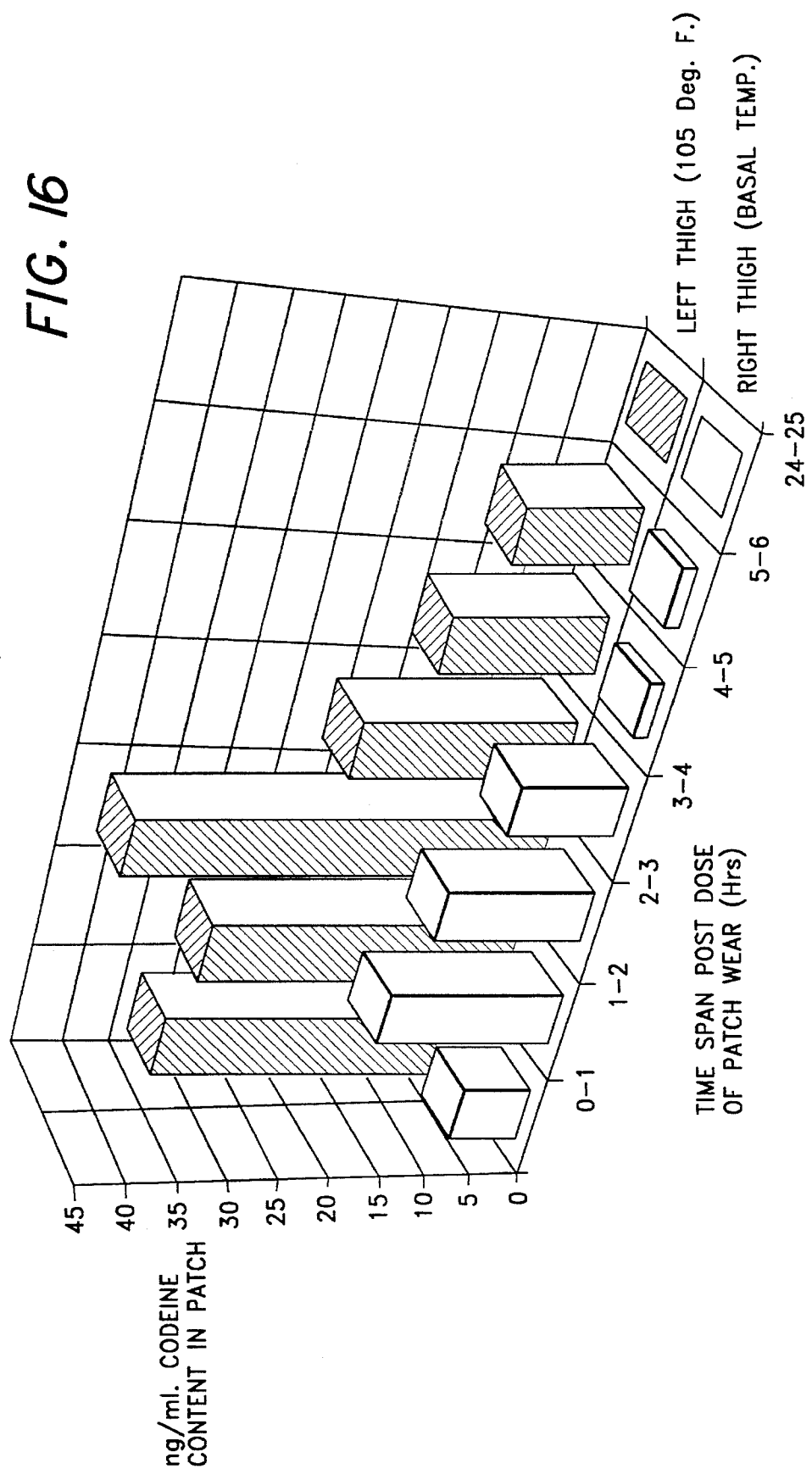
FIG. 16 is a graph showing the results of an experiment testing the effect of localized active perspiration on the collection of an analyte in a dermal patch.

The results of this experiment are shown in the graph of FIG. 16. From this graph, it can be seen that the patches applied to the thigh which was heated to 105° C. contained more analyte than the patches on the unheated thigh during the first six hours of the experiment. Thus, by inducing active perspiration in a subject, a desired amount of an analyte present in the subject's perspiration can be collected from the subject in a shorter period of time.

B. Heat Generation

In order to detect analytes contained in perspiration more rapidly, a dermal patch can be used which makes use of a heat generating means to raise the temperature of a subject's skin in the area where the patch is located. In this aspect of the present invention, the heat generating means is preferably capable of reaching a temperature of between about 100° F. and 150° F., and more preferably can be heated to between about 105° F. and 115° F. In one preferred embodiment, the heat generating means reaches a temperature of about 115° F. The temperature of the skin underneath the dermal patch should also be approximately within the foregoing temperature ranges when collecting perspiration according to this aspect of the present invention. Thus, it is advantageous to locate the heat generating means such that it is in contact with or is in very close proximity to the skin of a subject when the dermal patch is on a subject's skin.

In another aspect of the present invention, a subject can be made to actively perspire by raising the temperature of the interior of the subject's body rather than by applying heat to the subject's skin with an external heat generating means. By raising the internal temperature of a subject's body, the temperature of the surface of the subject's skin is also thereby increased. In this embodiment of the invention, a patch is placed on the surface of a subject's skin, after which the subject's core body temperature is raised such as through heavy excercise or through the administration of therapeutic agents which can raise the subject's body temperature. The perspiration which is generated by raising the subject's body temperature is then collected on the patch. Alternatively, the internal temperature of only a portion of a subject's body can be raised, and perspiration can then be collected by a patch placed on the skin of the portion of the subject's body which is being heated. For example, an insulating material can be wrapped around the thigh of a subject in order to increase the temperature of that subject's thigh, and a patch can be placed on the skin of the subject's thigh in order to collect perspiration. Thus, in this aspect of the present invention, the temperature of the surface of the skin beneath a patch is raised by using the body's own internal heat generating mechanisms, rather than by externally applying heat to a subject's skin as in other aspects of the present invention.

The temperature to which the surface of a subject's skin beneath a dermal patch should be raised in a particular aspect of the present invention is likely to vary, depending largely on the length of time within which an analyte is to be detected. When the skin temperature of a human subject is raised to about 115° F., sufficient perspiration (about 0.10 ml) can be collected in a patch of about 10 $cm^2$ within between about 20 minutes and one hour to allow the detection of an analyte. In general, the higher the temperature of the heat generating means, the higher the rate at which an analyte will be collected. Thus, heat generating means which reach temperatures higher than 150° F. can also be used to collect perspiration. However, temperatures which are high enough to cause burns or other skin damage, should not be produced by the heat generating means. Not only do such high temperatures cause injury to the subject from whom perspiration is being collected, but they are also likely to cause tissue damage which may interfere with the transport of perspiration.

One of skill in the art can perform routine experimentation to determine an appropriate temperature for collecting a desired amount of perspiration in a given amount of time. Such routine experimentation would likely include placing a patch having a predetermined area on a subject in a particular area of skin, bringing the temperature of the skin of the subject in that particular area to a specific temperature with a heat generating means, maintaining the patch on the subject's skin for the desired period of time, removing the patch after the desired period of time, and measuring the amount of an analyte contained in the patch. If the amount of analyte in the patch is found to be insufficient, the temperature of the heat generating means or the area of the patch can be increased in order to increase the amount of perspiration which flows into the patch, and thus the amount of an analyte which collects therein. Of course, one could also lengthen the amount of time the patch is in contact with the skin in order to increase the amount of analyte in the patch.

C. Energy-Assisted Dermal Patches

The derreal patches according to this aspect of the present invention can be constructed in much the same manner as other derreal patches disclosed herein. The distinctive feature of energy-assisted derreal patches is, however, that they include or are designed to operate with a heat generating means which raises the temperature of the patch and the surface of the skin near the patch. Therefore, the materials used to make energy-assisted dermal patches must be able to withstand the increased temperatures to which energy-assisted derreal patches are subjected.

Either occlusive or non-occlusive materials can be used to construct the outer layers in this aspect of the invention. This is because the detrimental effects of using an occlusive patch, such as the tendency of an occlusive patch to foster back-diffusion, are not significant over the short periods of time during which perspiration is collected using energy-assisted dermal patches.

A rate-limiting structure can be used in this aspect of the present invention if a quantitative determination of the amount of an analyte contained in perspiration is desired. Such a rate-limiting structure can be placed between the skin of the subject and the absorbent material of an energy-assisted derreal patch. As long as the rate of perspiration flow which such a structure allows is slightly less than the expected rate of perspiration of a subject at the temperature at which a particular energy-assisted patch operates, the approximate volume of perspiration which enters the patch can be determined by recording the amount of time that the patch is worn and then multiplying that amount by the rate at which the rate-limited structure allows perspiration to enter the patch. After then determining the amount of an analyte in the patch, the approximate concentration of the analyte in a subject's perspiration can be determined.

In a preferred embodiment, energy-assisted dermal patches are designed to be used only once. Such single use patches have the advantage of being convenient since they can be disposed of after use. Single-use patches are also more hygenic because they obviate the possibility that an allergen or infectious agent might be passed onto a subsequent user of part or all of an energy-assisted patch.

1. Electrical Heat Generating Means

The heat generating means according to this aspect of the invention can take various forms. In one embodiment, the heat generating means is an electrical device which uses electricity to generate heat (i.e., an electric heater). One such electrical heat generating means is an electrically heated pad, such as those commonly sold to relieve back or muscle pain. Such a pad can be placed over a dermal patch so that the pad overlies the patch. Preferably, the pad is large enough in area to also contact the skin surrounding the patch. The pad is then heated to an appropriate temperature, such as about 115° F., in order to produce sufficient perspiration to detect an analyte within a desired period of time.

In this embodiment, the dermal patch and heating pad can be made or sold together as a kit. Preferably, the pad is adapted to reversibly secure the dermal patch. After such a patch has been used to collect perspiration, it can be removed from the pad for analysis and replaced by a new patch.

In another embodiment, a derreal patch can include an electrically conductive heating element, such as a metal wire or mesh, which can be reversibly connected to a source of electricity. Such a heating element is preferably separated from the rest of the patch and from the skin of a subject wearing the patch by a material, such as a plastic material, which does not conduct electricity but does conduct heat. In this way, the element can be heated without exposing a wearer of the patch to electrical shock.

The electrically-powered heating means described herein can use either alternating or direct current. In a therapeutic setting, such as a medical office or hospital, the heating means can conveniently use alternating current drawn from a conventional electrical outlet by means of an electric cord. In an outdoor or other appropriate setting, however, a battery powered electrical heat generating means is likely to be more convenient.

2. Chemical Heat Generating Means

In another embodiment, the heat generating means of the energy-assisted dermal patches of the present invention can comprise a chemical composition which produces heat when it reacts. Such a chemical composition can be incorporated into a patch such as the patch shown in FIGS. 15A and 15B. Alternatively, the composition can be added to a patch after the patch has been placed on the skin of a subject.

One composition which can be used in this embodiment of the invention is disclosed in U.S. Pat. No. 3,976,049 to Yamashita, et al. (reissued as Reissue Patent RE 32,026). This composition is used in pocket hand warmers for skiing and the like, such as those marketed by John Wagner Associates, Inc. (Concord, Calif.). The composition comprises iron powder, a metal chloride or sulfate, activated carbon, and water, though the principal heat generating agent is the iron powder. As disclosed in the Yamashita patent, various iron powders can be used, including cast iron powder, reduced iron powder, and electrolytic iron powder.

The metal chloride or sulfate of the foregoing composition can, for example, comprise ferric sulfate, potassium sulfate, sodium sulfate, magnesium sulfate, potassium chloride, sodium chloride, calcium chloride, and magnesium chloride. These compounds enhance the reaction of the iron powder when it comes into contact with the oxygen in air. In addition, some of the chloride compounds, including calcium and magnesium chloride, can absorb water vapor, and thus help to prevent the escape of water vapor. This conserves the heat produced by the composition by preventing water vapor from carrying away such heat. These metal sulfates and chlorides are preferably present in the composition in an amount of between approximately 0.5–30 parts by weight per 100 parts by weight of iron powder.

Another ingredient of this heat generating chemical composition is activated carbon. This ingredient serves in part to absorb some of the water vapor released during the exothermic reaction which takes place when the composition is exposed to air, and thus also helps to retain the heat evolved during the reaction. Other porous materials, such as porous silicates, cotton, and wood powder, can be used in place of the activated carbon, however, if desired. Activated carbon is preferred over other materials though, because it also serves to absorb any odors released during the reaction of the chemical composition. When activated carbon is used in the present composition, it should be present in the range of about 2.5–400 parts by weight per 100 parts by weight of iron.

Water is also used in the composition. Water should be present in the range of approximately 10–250 parts by weight per 100 parts by weight of activated carbon. Other ingredients, such as catalysts of the oxidation of iron, can be added as well. For example, it has been found that the addition of small amounts of chromium, manganese, or copper to the iron powder greatly increases the oxidation of the iron. Such catalysts should be added in amounts of approximately 80–500 parts per million by weight, based on 100 parts by weight of iron powder.

In a preferred embodiment, the heat generating composition of Yamashita is present in a layered bag 220 within the dermal patch of the present invention. As shown in FIG. 15C, the chemical composition 223 in this embodiment is surrounded by an inner bag layer 221 which contains the composition 223 and allows air to reach it. The inner bag layer 221 can, for example, be made from cloth, such as cotton cloth or a synthetic cloth. This layer 221 should have an air permeability in the range of about 9,000–10,000 cubic centimeters of air per square centimeter of bag per minute ($cc/cm^2$-min.).

The outer bag layer 222 also helps to prevent the leakage of the composition 223 and in addition helps to prevent the vaporization of moisture from the bag. If vapor, such as water vapor, is allowed to escape from the bag layers 221 and 222 unimpeded, the composition 223 will tend to heat up more slowly, since the vapor will carry heat away from the patch. This outer bag layer 222 should have a lower air permeability compared to the inner bag layer 221 in order to help retain such water vapor.

Preferably, the outer bag layer 222 has an air permeability of about 0.5–400 $cc/cm^2$-min., and more preferably the outer bag layer 222 has an air permeability in the range of about 1–150 $cc/cm^2$-min. The outer bag layer 222 can, for example, be made of a plastic film such as polyethylene, polypropylene, nylon, polyester, polyvinyl chloride, polyvinylidene chloride, polystyrene, or rubber. Such plastic films should contain aeration holes over approximately 0.1%–5% of their surface areas so as to provide the requisite air permeability.

The composition should also, of course, be mixed while isolated from air or other sources of free oxygen so that it does not substantially oxidize before being incorporated into a dermal patch or before being used to raise the temperature of the skin of a subject wearing a derreal patch. Once mixed and formed into a layered bag, the composition should be sealed from the air until ready for use. If the composition is incorporated into a dermat patch, the entire patch should be encased in material which resists the influx of air, or at least of oxygen, until it is applied to the skin of a subject. A material such as cellophane can, for example, be used.

Other heat-producing chemical compositions can also be used according to the present invention. For example, the composition disclosed in U.S. Pat. No. 3,301,250 can be used instead of the composition described above. Other compositions known to those of skill in the art can be used as well.

FIGS. 15A–15C exemplify one possible patch according to the present invention. The patch 200 in this embodiment comprises an absorbent material 210, a layered bag 220 containing a chemical composition, and an outer protective layer 230. The absorbent material 210 is located underneath the protective layer 230 which, when the patch is worn on the skin 240 of a subject, is in contact with such skin. The protective layer 230 preferably has an adhesive composition applied thereto to aid in securing the patch 200 to the skin 240 of a subject.

In the embodiment shown in FIG. 15B, the absorbent material is circular in shape. However, the absorbent material can be formed into any convenient shape which has a large enough surface area to collect perspiration.

Surrounding the absorbent material of the patch of FIGS. 15A and 15B is a structure comprising a chemical composition 223 which is capable of generating heat when reacted. The composition can be the composition described above that comprises iron, water, a metal chloride or sulfate, and activated carbon which generates heat by an exothermic reaction when exposed to the air. In the embodiment shown in FIGS. 15A–15C, the layered bag 220 is positioned underneath the protective layer 230 and thus is in contact with the skin 240 of a subject wearing the patch. In this embodiment, the composition does not directly touch the skin of a subject wearing the patch, but rather is in contact with the skin through the bag so that any potential irritation to the subject's skin due to the chemical composition can be avoided.

Although the layered bag 220 is shown in FIGS. 15A and 15B as being underneath the protective layer 230, this is not critical. It is only necessary that the bag 220 be in close enough contact with the skin of a subject when the patch is worn that the heat generated by the chemical composition 223 is sufficient to increase the rate of perspiration of the subject. In addition, while the layered bag 220 is depicted in FIG. 15B as being circular, this also is not critical. Thus, the bag 220 can also be positioned above the protective layer 230 and can be formed into other shapes.

If the composition is one which will not interfere with the detection or collection of an analyte of interest, the composition 223 can alternatively be distributed within the absorbent material 210. In some embodiments, a layered bag may not even be necessary.

One particular advantage of using chemical heat generating means in the energy-assisted dermal patches of the present invention is that patches with chemical heat generating means can be designed to be single use patches where both the patch and the heat generating means can be economically disposed of after a single use. The patch illustrated in FIGS. 15A–15C is an example of such a single use patch. This patch can be stored in an air-tight package until needed. Once removed from the package and exposed to oxygen in the air, the chemical composition described above which is contained in the layered bag 220 will begin to react and heat up. The patch is then quickly placed on a subject from whom a sample of perspiration is desired.

After a desired amount of perspiration has been collected from the subject, the patch is removed from the surface of the subject's skin, and the perspiration in the patch is analyzed. The entire patch, including the chemical heat generating means, is then disposed of. The chemical reactants of the chemical heat generating means cannot be easily regenerated, and the absorbent material of the patch is contaminated with the analytes of the subject from whom perspiration was collected after use. Therefore, disposal of the used patch and the chemical heat generating means is the only practical disposition of the used patch components.

IX. Determining Allergic Sensitivity with a Dermal Patch

A. Derreal Allergic Reactions

In a further aspect of the present invention, a patch can be used to determine whether a subject is allergic to a particular allergen. Allergens include various forms of pollen, dust, animal skin and fur, chemicals such as insecticides or food additives, and foods. The presence of an allergen on the skin of an individual sensitive to that allergen causes an immune system reaction, known as an allergic reaction, in that individual.

Certain components of the immune system involved in provoking an allergic reaction, such as IgE, complement, and various immune cells, are believed to be able to migrate in the dermis. Components of the immune system also circulate in the blood supplying the skin, and as part of an allergic reaction to an allergen on the skin the permeability of the blood vessels supplying the skin is increased. Immune components of the blood are thereby also believed to participate in a dermal allergic reaction. Thus, the presence of an allergen on the skin results in the migration and concentration of immune components of the body on the surface of the skin where the allergen is present.

B. Using Dermal Patches to Determine Allergic Sensitivity

A subject, preferably a mammal, can be tested for its sensitivity to an allergen by contacting an allergen to the skin of the subject and then detecting any immune components which pass through the skin of the subject and onto a patch of the present invention. In this embodiment, a patch is used which contains an allergen in fluid communication with the skin of the subject when the patch is worn on the skin of the subject. For example, the allergen can be contained in the absorbent material of the patch.

In a preferred embodiment, an agent is also present in the patch in fluid communication with the skin of a wearer of the patch. The agent is one capable of increasing the permeability of the capillaries in the subject's dermis. Such an agent can thus increase the permeability of the capillaries in the dermis beneath the patch and facilitate the flow of immune components to the site of the allergen.

To determine whether a subject is allergic to a particular allergen, a patch of the present invention which additionally includes an allergen is placed on the surface of the skin of the subject. In this embodiment, when perspiration reaches the patch, the allergen is in fluid communication with the skin of the subject and contacts the skin so as to cause an allergic reaction in the subject, if the subject is sensitive to the allergen. The patch will then be able to collect bodily components on the absorbent material of the patch which are associated with an allergic reaction, such as immune system components, which migrate to the location of the allergen. Once such components have accumulated in the absorbent material, the patch is removed, and the presence of such components is detected. If such allergic reaction-associated components are present on the patch, this is indicative that the subject is allergic to the allergen tested.

Alternatively, the skin of the subject can be exposed to an allergen in any other way, such as simply by placing a sample of the allergen on the skin of the subject. Perspiration and other components expressed through the skin can then be accumulated in a patch of the present invention located proximate to the area of the skin of the subject which was exposed to the allergen. If an analyte indicative of an allergic reaction is then detected in the perspiration accumulated on the patch, the subject can be diagnosed as being allergic to the allergen.

The patch used in this embodiment of the present invention can be any of the types previously described. Preferably, a specific binding partner capable of binding and concentrating particular bodily components indicative of an allergic reaction are included in the absorptive layer (or concentration zone) of this aspect of the present invention.

As an example of the present embodiment of the invention, an antigen such as pollen can be placed in the absorptive layer of the patch so that when perspiration penetrates the absorptive layer and brings moisture to that layer, the allergen can migrate through the absorptive layer to the lower surface of the patch in contact with the skin and provoke an allergic reaction, if the subject is prone to develop an allergic reaction to the allergen. Alternatively, the allergen can be placed directly on the lower surface of the patch so that it immediately comes into contact with the skin of a subject wearing the patch.

After an immune response is triggered in a subject who is allergic to the allergen, components involved in the response will increase in concentration in the vicinity of the patch, since it is the site of the allergen. As sensible and insensible perspiration pass through the skin and into the patch, the immune components which pass through the skin with such perspiration concentrate on the absorptive layer of the patch.

Agents which increase capillary permeability in the dermis immediately beneath the patch are preferably included in the patch. Molecules circulating in the capillaries beneath the skin can thereby be made to diffuse into the interstitial space of the skin and from there into perspiration. Such perspiration can then carry these molecules into the patch so that they can be detected.

The following examples describe only specific applications of the present invention.

EXAMPLE 1

Preparation of Monoclonal Antibodies to CK-MB for Use on a Test Patch

In accordance with one known process for preparing monoclonal antibodies, mice such as Balb/c female mice or other mouse strains or even other suitable animals such as rats or rabbits are immunized with an amount of the CK-MB enzyme to initiate an immune response. The enzyme dosage and immunization schedule for producing useful quantities of suitable splenocytes can be readily determined depending on the animal strain used.

The size and spacing of doses of CK-MB or other antigen are of prime importance in the antibody response. Fortunately, a wide range of antigen doses commonly affords immunity against harmful agents. Thus, a small dose of antigen is usually sufficient to initiate an antibody response, i.e., microgram quantities of proteins are frequently adequate. However, a minimum dosage for initiating an immune response does typically exist, although doses of antigert below the minimum dose necessary to initiate an antibody response will usually maintain antibody production which is already in process. For example, an initial immunization with approximately 50 μg of the enzyme may be followed by a hyperimmunization series of five injections.

When certain compounds which are themselves not necessarily antigenic are mixed with an antigen, enhanced antibody production against the antigen occurs, as evidenced by the appearance of large amounts of antibody in the serum, a prolonged period of antibody production, and a response to lower doses of antigen. Such substances are called "adjuvants" and include Freund's incomplete and complete adjuvants and alum gels. Thus, a given dose of antigen is usually more effective when injected subcutaneously with an adjuvant or when injected as repeated small aliquots than when administered intravenously.

Typically, the adjuvants of Freund are preferred. The original "complete" Freund's adjuvant mixture consists of mineral oil, waxes and killed tubercle bacilli. Antigen is added to the adjuvant mixture in an aqueous phase to form a water-in-oil emulsion in which each water droplet is surrounded by a continuous oil phase containing tubercle bacilli. The mixture is commonly injected subcutaneously into experimental animals. Injection stimulates a marked granulomatous reaction with lesions consisting largely of collections of histiocytes, epithelioid cells and lymphocytes. The local lymph node shows a small increase in plasma cells.

Following the immunization with a primary dose of a soluble protein antigen, specific antibodies normally first appear in the serum after a few days and then increase in number until about the second week. Thereafter, the number of serum antibodies slowly declines over a period of weeks to months.

The first serum antibodies to appear after antigenization are IgM antibodies. These are usually followed by the appearance of IgG antibodies. Later, as antibody serum levels increase, IgM antibodies disappear, probably as a result of specific feedback suppression of IgG antibodies.

After the "primary response" to a protein has passed, a second dose of the same antigen given months or even years later usually elicits an intense and accelerated "specific secondary response" in which serum antibody usually begins to rise within two or three days of exposure. The serum levels of antibody in a secondary response may reach as high as 10 mg per ml.

The animal is subsequently sacrificed and cells taken from its spleen are suspended in an appropriate medium and fused with myeloma cells, such as those obtainable from the murine cell line Sp2/O-Ag14. The result is hybrid cells, referred to as "hybridomas," which are capable of reproduction in vitro and which produce a mixture of antibodies specific to each of the various recognizable sites on the CK-MB enzyme.

The myeloma cell line selected should be compatible with the spleen cells, and optimally should be a cell line of the same species as the spleen cells. Although the murine cell line Sp2/O-Ag14 has been found to be effective for use with mouse spleen cells, other myeloma cell lines can alternatively be used. See, for example, Nature, 276: 269–270 (1978).

The myeloma cell line used should preferably be of the so-called "drug resistant" type, so that any unfused myeloma cells will not survive in a selective medium, while hybrid cells will survive. A variety of drug resistant myelomas are known.

The mixture of unfused spleen cells, unfused myeloma cells and fused cells are diluted and cultured in a selective medium which will not support the growth of the unfused myeloma cells for a time sufficient to allow death of all unfused cells. A drug resistant unfused myeloma cell line will not survive more than a few days in a selective medium such as HAT (hypoxanthine, aminopterin and thymidine). Hence, the unfused myeloma cells perish. Since the unfused spleen cells are nonmalignant, they have only a finite number of generations until they fail to reproduce. The fused cells, on the other hand, continue to reproduce because they possess the malignant quality contributed by the myeloma parent and the enzyme necessary to survive in the selected medium contributed by the spleen cell parent.

The supernatant from each of a plurality of hybridoma containing wells is evaluated for the presence of antibody to a specific site unique to the CK-MB enzyme structure. Hybridomas are then selected producing the desired antibody to that specific site. This selection may be, for example, by limiting dilution, in which the volume of diluent is statistically calculated to isolate a certain number of cells (e.g., 1 to 4) in each separate well of a microliter plate. In this way, individual hybridomas may be isolated for further cloning.

Once the desired hybridoma has been selected, it can be injected into host animals of the same species as those used to prepare the hybridoma, preferably syngeneic or semi-syngeneic animals. Injection of the hybridoma will result in the formation of antibody producing tumors in the host after a suitable incubation time, resulting in a very high concentration of the desired antibody in the blood stream and in the peritoneal exudate of the host. Although the hosts have normal antibodies in their blood and exudate, the concentration of these normal antibodies is only about 5% of the concentration of the desired monoclonal antibody. The monoclonal antibody may then be isolated in accordance with techniques known in the art.

EXAMPLE 2

Preparation of Microbead Test Patch

One specific application of the present invention is the dual determination of skeletal muscle and cardiac muscle status as a result of exercise. A dermal patch is constructed in accordance with the embodiment illustrated at FIGS. 3 and 3a. The gauze layer is prepared by cutting a circular patch having an approximately 1-inch diameter from a Johnson & Johnson non-stick gauze pad. The inner and outer porous layers are next prepared by cutting two circular patches of Ultipor (nylon 6), from Pall Corporation in Glen Cove, N.Y. Ultipor membrane is both fluid permeable and microporous, and a membrane is selected having, for example, a 1 micron rating. The microbead layer is prepared by covalently bonding monoclonal antibody raised against CK-MB to a multiplicity of polystyrene beads having a mean particle size of at least about 10 microns.

The patch is assembled by distributing approximately 0.2 gram of microbeads across the surface of one of the porous layers. The second porous layer is thereafter disposed adjacent the microbeads, and the gauze layer is next placed on top of the second porous layer. At this point, the patch is upside-down. The peripheral edges of each of the first and second porous layers and the gauze layers are secured together by conventional heat-sealing techniques. Thereafter, the subassembly is turned over and an annular torus of adhesive tape having approximately a 2-inch outside diameter and slightly less than a 1-inch inside diameter is secured thereto to produce a finished patch.

EXAMPLE 3

Cardiac Muscle Status Test

The patch of Example 1 is then secured to the chest of a healthy 40-year old male and worn throughout a 36-mile (130-minute) bicycle ride. Upon removal of the patch following the ride, the test patch is immersed in a first solution containing an excess of enzyme labeled anti-CK-MB for approximately 30 minutes, to permit conjugation of labeled antibody with immobilized analyte. The patch is then rinsed under tap water to remove unbound labeled antibody and immersed in a second solution containing a substrate for the bound enzyme label, which undergoes a color change when acted upon by the enzyme. Appearance of color through the top porous layer indicates the presence of CK-MB, and possible cardiac injury. Comparison to a color chart permits rough quantification.

EXAMPLE 4

Test for Use of Marijuana

THC polyclonal antibody from sheep (available from Biogenesis, Bournmouth, England) is diluted 1:100 in PBS (pH 7.5). The antibodies are bound to Gelman 0.45μ (SU-450) Ultrabind Supported Membrane, following the protocol in Gelman Original Equipment Manufacturer application P.N. 31,084. The membranes are air dried. Disks, ⅜ inch in diameter, are cut from the coated Gelman membranes. These ⅜ inch disks are mounted at the center of a ¼ inch diameter hole cut in the center of a one inch diameter circle of Tegaderm 1625 Transparent Dressing (available from Minnesota Mining and Manufacturing, St. Paul, Minn.).

Three mounted membranes are secured to the chest of a subject who then smokes a marijuana cigarette. Three mounted membranes are also secured to a subject who has never used marijuana in any form and who agrees not to use it for the next seven days. The membranes remain in place until they are removed, seven days later. Each of the removed membranes is flushed five times with 300 µl of 0.2% Tween 20 in PBS. The membranes are incubated for 30 minutes in 100 µl of E-Z Screen Cannabinoid enzyme conjugate from the E-Z Screen Test Kit (available from Environmental Diagnostics, Inc., Burlington, N.C.).

After incubation, each membrane is flushed three times with 300 µl of 0.2% Tween 20 in PBS, followed by three flushes with PBS alone. The membranes are then incubated in TMB Membrane Peroxide Substrate (available from Kirkegaard & Perry Labs, Gaithersburg, Md.) for 10 minutes. A light blue background appears in all six membranes. White dots appear over the background on the three membranes taken from the subject who smoked a marijuana cigarette, indicating sweat gland output of sweat containing THC derivatives. No white dots appear on the three membranes taken from the subject who has never used marijuana.

EXAMPLE 5

Positive Control Patch

Mouse anti-human IgG, Fc monoclonal antibody (available from ICN, Costa Mesa, Calif.) is diluted 1:100 in PBS (pH 7.5). The antibodies are bound to Gelman 0.45µ (SU-450) Ultrabind Supported Membrane, following the protocol in Gelman Original Equipment Manufacturer application P.N. 31,084. The membranes are air dried. Disks, ⅜ inch in diameter, are cut from the coated Gelman membranes. These ⅜ inch disks are centered and mounted on a ¼ inch diameter hole cut in the center of a one inch diameter circle of Tegaderm 1625 Transparent Dressing.

Three mounted membranes are secured to the chest of five human subjects. The membranes remain in place until they are removed, seven days later. Each of the removed membranes is flushed five times with 300 µl of 0.2% Tween 20 in PBS. The membranes are incubated for 30 minutes in 100 µl of Horseradish peroxidase enzyme conjugated to goat anti-human IgG, Fc polyclonal antibody (available from ICN, Costa Mesa, Calif.) diluted 1:1000 in PBS.

After incubation, each membrane is flushed three times with 300 µl of 0.2% Tween 20 in PBS, followed by three flushes with PBS alone. The membranes are then incubated in TMB Membrane Peroxide Substrate (available from Kirkegaard & Perry Labs, Gaithersburg, Maryland) for 10 minutes. Blue dots corresponding to individual sweat ducts appear over the background on all of the membranes, indicating that the chemistry of the patches is operative by their detection of the IgG expected in the sweat of all subjects.

EXAMPLE 6

Chemical Modification of Cocaine Collected on a Patch

Absorption disks, ⅜ inch in diameter, are cut from Gelman membranes (Gelman 0.45µ (SU-450) Ultrabind Supported Membranes). These ⅜ inch disks are mounted at the center of a ¼ inch diameter hole cut in the center of a one inch diameter circle of Tegaderm 1625 Transparent Dressing (available from Minnesota Mining and Manufacturing, St. Paul, Minn.) to form a patch.

Three of such patches are secured to the chest of a subject who then ingests cocaine. Three patches are also secured to a subject who has never used cocaine in any form and who agrees not to use it for the next seven days. The patches remain in place until they are removed seven days later from each subject.

The cocaine molecules and other components present in the membranes of each patch are then eluted from the membranes by soaking each of the membranes in a synthetic urine matrix for 30 to 60 minutes at room temperature with mechanical agitation to form an analyte solution. Following elution, the analyte solutions derived from each of the patches are brought to a pH of 11 by the addition of NaOH to each of the solutions. The solutions are reacted for 20 minutes at pH 11 and at room temperature, after which the solutions are neutralized with HCl.

Each solution is then subjected to diagnostic analysis with the Roche RIA system (Nutley, N.J.) for detecting the metabolite of cocaine BE. The subject who ingested cocaine tests positive for the cocaine metabolite BE, while the subject who did not consume cocaine over the test period does not test positive for BE.

EXAMPLE 7

Preparation and Use of a Dissolvable Absorption Disk

Nylon 6/6 fibers (Vydyne 909 from Monsanto Co.) are formed into an absorbent gauze. Disks approximately ⅜ inch in diameter are cut from such gauze and are then mounted at the center of a ¼ inch diameter hole cut in the center of a one inch diameter circle of Tegaderm 1625 Transparent Dressing (available from Minnesota Mining and Manufacturing, St. Paul, Minn.) to form a patch. Such a patch is then applied to a subject. The subject is directed to ingest cocaine, and a quantity of perspiration is then allowed to accumulate on the patch.

When a sufficient period of time has passed for a detectable amount of cocaine to accumulate on the patch, the patch is removed from the subject and placed in an insoluble container. A base capable of dissolving the Nylon 6/6 fibers is then poured over the patch. Once the nylon absorption disk is dissolved, the undissolved components of the patch are removed from the container. Since cocaine is converted into benzoylecgonine (BE) in the presence of a base, the cocaine contained in the disk is metabolized to BE when the disk is dissolved.

The solution of the dissolved nylon, BE, and the other remaining components of the used absorption disk are next neutralized. This solution is then analyzed using a Roche RIA system (Nutley, N.J.). The BE in the solution is detected and the amount of BE concentrated in the absorption disk is determined.

EXAMPLE 8

Quantitative Determination of a Component of Perspiration

To determine how much of an analyte is contained in a given volume of sweat, a patch is first constructed having a support layer made from a polyester-supported polycarbonate microporous membrane, manufactured by Nuclepore (Menlo Park, Calif.). Over this is placed an absorbent material such as Filtration Sciences medical grade paper (FS#39) for accumulating and concentrating perspiration. The surface area of the layer of absorbent material should be the same as or smaller than that of the support layer so that when placed on a subject's skin, only the support layer is in contact with the subject's skin. Over this layer is then placed an outer protective layer made of 1625 Tegaderm wound dressing made by the 3M Company (St. Paul, Minn.). This outer layer is of a larger surface area than either the support layer or the absorbent material and covers both of these layers. The outer layer separates the absorbent material from the outside of the patch and helps prevent perspiration from entering the absorbent layer except through the support layer. The outer perimeter of the outer layer has an adhesive on the side of the outer layer that faces the skin of a subject when the patch is applied to the skin of such a subject in order to secure the patch.

Such a patch is next placed on the skin of a subject whose perspiration is to be tested for the presence of theophylline. The subject wears the patch for 7 days, during which time perspiration passes through the support layer at a rate of less than 6 grams/m$^2$/hour. After this the patch is removed and subjected to analysis to determine the amount of theophylline contained in the patch.

To determine the volume of sweat that has passed into the absorbent material of the patch, the rate at which perspiration passed into the absorbent material is multiplied by the amount of time the patch was worn, i.e., 7 days. The amount of theophylline contained in the patch is then determined. These numbers are then related in order to determine the amount of analyte contained in a given volume of perspiration by dividing the amount of the analyte in the patch by the volume of perspiration which passed through the support layer into the absorbent material.

EXAMPLE 9

Preparation and Use of a Dermal Patch to Determine the Sensitivity of a Subject to an Allergen In order to determine whether an individual is allergic to cat hair, a preparation containing cat hair is first placed on the lower surface of a disk ⅜ inch in diameter made of Filtration Sciences medical grade paper (FS#39). The upper surface of the disk is mounted at the center of a ¼ inch diameter hole cut in the center of a one inch diameter circle of Tegaderm 1625 Transparent Dressing (available from Minnesota Mining and Manufacturing, St. Paul, Minn.). The patch is then placed on the surface of the skin of a human subject for approximately 3 days in order to accumulate perspiration on the disk and form a concentrate. The disk is then removed and analyzed to detect IgA against cat hair. The presence of IgA against cat hair indicates that the subject has expressed an allergic reaction to the cat hair antigen.

Although this invention has been described in terms of certain preferred embodiments and assay schemes, other embodiments and assays that are apparent to those of ordinary skill in the art are also within the scope of this invention. Accordingly, the scope of the invention is intended to be defined only by reference to the appended claims.

EXAMPLE 10

Constructing a Dermal Patch which Inhibits Back-Diffusion

Absorption disks, ⅜ inch in diameter, are first cut from Gelman membranes (Gelman 0.45μ (SU-450) Ultrabind Supported Membranes). These absorption disks are next soaked in a buffer of 0.1M acetic acid at a pH of 5.0, and the disk is allowed to dry. The ⅜ inch disks are then mounted at the center of a ¼ inch diameter hole cut in the center of a one inch diameter circle of Tegaderm 1625 Transparent Dressing (available from Minnesota Mining and Manufacturing, St. Paul, Minn.) to form a patch. The buffer-soaked absorption disk could also be mounted onto the Tegaderm dressing while still wet.

EXAMPLE 11

Preventing the Back-Diffusion of a Drug of Abuse

A patch is constructed according to Example 10. The buffer is added to the absorptive layer (absorption disk) of the patch in order to keep the pH of the patch and the surface of a subject's skin below the patch in the range of 4.5–5.0. When the patch is placed on the skin of the subject who has ingested one of the drugs of abuse listed in Table 2 (above), the patch concentrates the particular drug ingested, without any substantial back-diffusion.

EXAMPLE 12

Quantitatively Determining the Amount of an Analyte Present in a Subject

A patch is constructed according to the method of Example 10 with an absorption disk having a surface area of 10 cm$^2$. This patch is then placed on the biceps of a subject's arm. The subject, weighing 168 pounds, is given 126 mg of cocaine, which is subsequently nasally ingested. The patch is worn for approximately 200 hours, and the subject is not allowed to ingest any more cocaine. After 200 hours the patch is removed in order to determine how much cocaine has been collected. In this experiment, approximately 500 ng (0.5 mg) of cocaine is recovered on the patch.

EXAMPLE 13

Preparation of a Heat Generating Chemical Composition and a Layered Bag

The following ingredients were prepared and mixed without substantially exposing them to the air:

| Material | Amount |
| --- | --- |
| Cast Iron Powder | 30 mg |
| Ferric Sulfate | 5 mg |
| Active Carbon | 30 mg |
| Water | 30 mg |

After mixing, the resulting composition was placed on a piece of cloth made from cotton that is about 4" long and about ½" wide. The cloth should be about 1 mm thick and allow air to pass through it at a rate of approximately 500 cc/cm$^2$-min.

This cloth is itself on top of a piece of polyethylene film that is slightly longer and wider than the cloth bag. The film is pre-drilled with holes of sufficient size and number to allow air to permeate the film at a rate of approximately 4 cc/cm$^2$-min.

The composition is spread evenly over the surface of the piece of cloth, and the film and cloth are then folded along their short axes so as to form a relatively long tube that is approximately circular in diameter. Any excess amount of the chemical composition that will not fit within this tube is removed and saved for later use. The exposed edges of the film are then sealed with heat or with an adhesive so as to encase the chemical composition within the cloth and film.

EXAMPLE 14

Preparation of an Energy-Assisted Dermal Patch which Uses Chemical Heat Generating Means A round disk made of an absorbent material is first constructed by cutting a portion of a Gelman membrane (Gelman 0.45μ (SU-450) Ultrabind Supported Membranes) which is ⅜ inch in diameter. This disk is then placed in the center, on the adhesive side, of a one inch diameter circle of Tegaderm 1625 Transparent Dressing (available from Minnesota Mining and Manufacturing, St. Paul, Minn.). The tube formed from polyethylene film, cloth, and the chemical composition of Example 13 is then placed around the edges of the disk, generally in the manner shown in FIGS. 15A and 15B, in order to form a patch. The entire patch is then quickly sealed from the air by surrounding it with cellophane film.

EXAMPLE 15

Using an Energy-Assisted Dermal Patch which Makes Use of Chemical Heating Means

The patch of Example 14 is removed from the air-tight cellophane package in which it is wrapped and is immediately placed on the arm of a subject. The temperature of the patch and the surface of the skin underneath the patch rises to over 100° F., and the patch is maintained on the skin of the subject for about one hour. The patch is then removed from the subject's skin and is analyzed in order to detect the presence of an analyte of interest in the patch.

EXAMPLE 16

Using a Subject's Body Heat to Accelerate the Collection of Perspiration with a Dermal Patch A dermal patch is constructed by first forming a round disk made of an absorbent material which is ⅜ inch in diameter. Such a disk is cut from a portion of a Gelman membrane (Gelman 0.45μ (SU-450) Ultrabind Supported Membranes). This disk is then placed in the center, on the adhesive side, of a one inch diameter circle of Tegaderm 1625 Transparent Dressing (available from Minnesota Mining and Manufacturing, St. Paul, Minnesota), thereby forming a dermal patch. This patch is then placed in contact with the thigh of a subject, and an insulating material is wrapped around the subject's thigh on top of the patch. The temperature of the subject's thigh increases, and the subject actively perspires. After about two hours, the patch is removed from underneath the insulating material, and the perspiration which has collected on the patch is analyzed in order to detect an analyte of interest.

EXAMPLE 17

Using an Energy-Assisted Dermal Patch which Makes Use of an Electric Heating Pad The patch of Example 16 is placed on the skin of a subject's arm. An electric heating pad with a sufficient area to cover the patch and also wrap around the circumference of the subject's arm is then placed over the patch and wrapped around the subject's arm. The heating pad is heated to about 120° F. and left on the subject's arm for approximately one hour. The patch is then removed from the subject's arm and is analyzed for the presence of an analyte of interest.

EXAMPLE 18

Use of Energy-Assisted Dermal Patches in Drug of Abuse Testing

The patch of Example 14 is removed from its air-tight packaging and is placed on the surface of the arm of a subject who has caused a fatal traffic accident. The chemical composition heats the skin for about 30 minutes. During this time, eccrine glands and other sweat glands produce perspiration, and this perspiration flows through the ducts, to the surface of the skin and into the absorbent material of the patch. After 30 minutes, the patch is removed and transported to a lab. The patch is then analyzed to determine whether a drug of abuse was present in the subject's perspiration.

EXAMPLE 19

Use of Energy-Assisted Derreal Patches in Medical Diagnoses

The patch of Example 14 is removed from its air-tight packaging and is placed on the surface of the arm of a subject who has been taking theophylline. The chemical composition heats the skin of the subject around the patch, and the patch is left on the subject's arm for about an hour. The patch is then removed and analyzed to determine the concentration of theophylline in the subject's perspiration. If the concentration of theophylline is higher than a desired concentration, the dose of theophylline which the patient is taking is lowered.

The foregoing examples and specific embodiments are meant to be exemplary only and do not limit the scope of the present invention. In addition, the references cited herein are hereby incorporated by reference.

What is claimed is:

1. A method of collecting an analyte contained in the perspiration of a mammal using a dermal patch, comprising the steps of:

a. placing a dermal patch on the skin of a mammal, wherein said patch comprises an absorbent material for collecting analytes contained in the perspiration of said mammal;

b. generating heat by means of a chemical composition in order to heat the skin of said mammal underneath said dermal patch, wherein perspiration flows through the skin of said mammal c. collecting an analyte present in the perspiration of said mammal in said absorbent material of said patch;

d. removing said patch after a sufficient period of time has elapsed following the initial application of heat to the skin of said mammal to allow said analyte to be detected in said patch by an assay for said analyte; and e. detecting the presence of said analyte in said patch.

2. The method of claim 1, wherein step (b) further comprises exposing a chemical composition to oxygen, wherein said chemical composition reacts exothermically in the presence of oxygen.

3. The method of claim 1, wherein step (b) comprises heating the skin of said mammal to between about 100° F. and 150° F.

4. The method of claim 3, wherein step (b) comprises heating the skin of said mammal to between about 105° F. and 115° F.

5. The method of claim 1, wherein step (d) comprises removing said patch after between 1 and 2 hours.

6. The method of claim 2, wherein step (d) comprises removing said patch after about 1 hour.

7. The method of claim 1, wherein step (d) comprises removing said patch after less than 1 hour.

8. The method of claim 1, wherein step (e) comprises detecting the presence of cocaine in said patch.

9. The method of claim 1, wherein step (a) comprises placing said dermal patch on the palm of one of said mammal's hands.

10. The method of claim 1, wherein step (a) comprises placing said dermal patch on the sole of one of said mammal's feet.

11. The method of claim 1, wherein step (a) comprises placing said dermal patch on facial skin of said mammal.

12. A single use dermal patch for detecting an analyte contained in the perspiration of a subject mammal, said patch comprising:

an outer protective layer having an adhesive applied to one side of said layer, wherein said adhesive secures said outer protective layer to the skin of a subject mammal when said patch is worn on the subject's skin;

an absorbent material for collecting analytes contained in the perspiration of said subject, wherein said absorbent material is secured to the side of said outer protective layer to which said adhesive is applied, said absorbent material being in fluid communication with the skin of said subject when said patch is worn on the subject's skin; and a heat-generating chemical composition, wherein said composition is secured to said outer protective layer or to said absorbent material of said patch, said composition being capable of reaching temperatures in excess of 105° F. when reacted.

13. The patch of claim 12, wherein said composition is one which reacts exothermically when exposed to air.

14. The patch of claim 12, wherein said composition comprises iron, a metal chloride or metal sulfate, activated carbon, and water.

15. The patch of claim 12, wherein said composition is further contained in a porous bag in said patch.

16. The patch of claim 12, wherein said chemical composition surrounds said absorbent material of said patch.

17. The patch of claim 12, wherein said outer protective layer comprises a layer of 1625 Tegaderm wound dressing.

18. The patch of claim 12, wherein said outer protective layer is rectangular.

19. The patch of claim 12, wherein said absorbent material is rectangular.

20. A packaged patch, comprising the patch of claim 12 and a package for said patch, wherein said package is made from a material that is resistant to the influx of air, and wherein said patch is encased in said package.

* * * * *

UNITED STATES PATENT AND TRADEMARK OFFICE
CERTIFICATE OF CORRECTION

PATENT NO. : 5,465,713

DATED : November 14, 1995

INVENTOR(S) : Donald Schoendorfer

It is certified that error appears in the above-indentified patent and that said Letters Patent is hereby corrected as shown below:

Column 2, line 13 change "from derreal patches" to --from dermal patches--

Column 2, line 36 change "the derreal surface" to --the dermal surface--

Column 2, line 41 change "the derreal collection" to --the dermal collection--

Column 2, line 48 change "Another derreal" to --Another dermal--

Column 2, line 55 change "art derreal" to --art dermal--

Column 4, line 47 change "view of a derreal" to --view of a dermal--

Column 4, line 51 change "the derreal patch" to --the dermal patch--

Column 5, line 2 change "of a derreal" to --of a dermal--

Column 5, line 15 change "derreal patch" to --dermal patch--

Column 5, line 21 change "which a derreal" to --which a dermal--

UNITED STATES PATENT AND TRADEMARK OFFICE
CERTIFICATE OF CORRECTION

PATENT NO. : 5,465,713

DATED : November 14, 1995

INVENTOR(S) : Donald Schoendorfer

It is certified that error appears in the above-indentified patent and that said Letters Patent is hereby corrected as shown below:

Column 10, line 27 change "E. Derreal Patches" to --E. Dermal Patches--

Column 13, line 4 change "II. Placement of Derreal Patches" to --II. Placement of Dermal Patches--

Column 14, line 41 change "B. Placement of Derreal Patches" to --B. Placement of Dermal Patches--

Column 14, line 64 change " III. Chemical Species Detectible with a Derreal Patch" to --III. Chemical Species Detectible with a Dermal Patch--

Column 16, line 21 change "Milsrein" to --Milstein--

Column 18, line 64 change "also be pedormed" to --also be performed--

Column 19, line 66 change "of lo polystyrene" to --of polystyrene--

Column 20, line 14 change "A. Derreal Patches" to --A. Dermal Patches--

Column 21, line 34 change "the derreal" to --the dermal--

Column 23, line 23 "into a derreal" to --into a dermal--

Column 23, line 26 "on a derral" to --on a dermal--

UNITED STATES PATENT AND TRADEMARK OFFICE
CERTIFICATE OF CORRECTION

PATENT NO. : 5,465,713

DATED : November 14, 1995

INVENTOR(S) : Donald Schoendorfer

It is certified that error appears in the above-indentified patent and that said Letters Patent is hereby corrected as shown below:

Column 23, line 26 "on a derral" to --on a dermal--

Column 23, line 33 "on a derreal" to --on a dermal--

Column 23, line 40 "on a derreal" to --on a dermal--

Column 23, line 43 "into a derreal" to --into a dermal--

Column 23, line 58 "on the derreal" to -- on the dermal--

Column 23, line 66 "the derreal" to --the dermal--

Column 24, line 11 "of the derreal" to --of the dermal--

Column 24, line 20 "of a derreal" to --of a dermal--

Column 25, line 4 "backdiffusion" to --back-diffusion--

Column 25, line 9 "of the derreal" to --of the dermal--

Column 25, line 10 change "of the sudace" to --of the surface--

Column 25, line 27, change "below a derreal" to --below a dermal--

Column 25, line 29, change "stratum cornlure" to --stratum cornium--

Column 26, line 19, change "stratum cornlure" to --stratum cornium--

UNITED STATES PATENT AND TRADEMARK OFFICE
CERTIFICATE OF CORRECTION

PATENT NO. : 5,465,713

DATED : November 14, 1995

INVENTOR(S) : Donald Schoendorfer

It is certified that error appears in the above-indentified patent and that said Letters Patent is hereby corrected as shown below:

Column 26, line 33, change "on the sudace" to --on the surface--

Column 26, line 39, change "nonionized" to --non-ionized--

Column 27, line 33, change "backdiffusion" to --back-diffusion--

Column 28, line 41, change "with Derreal" to --with Dermal--

Column 28, line 51, change "A. Derreal" to --A. Dermal--

Column 30, line 12, change "B. Derreal" to --B. Dermal--

Column 34, line 36 change "A derreal patch" to --A dermal patch--

Column 36, line 59 change "The derreal" to --The dermal--

Column 36, line 61 change "other derreal" to --other dermal--

Column 36, line 62 change "assisted derreal" to --assisted dermal--

Column 37, line 14 change "assisted derreal" to --assisted dermal--

Column 37, line 51 change "a derreal" to --a dermal--

UNITED STATES PATENT AND TRADEMARK OFFICE
CERTIFICATE OF CORRECTION

PATENT NO. : 5,465,713
DATED : November 14, 1995
INVENTOR(S) : Donald Schoendorfer It is certified that error appears in the above-indentified patent and that said Letters Patent is hereby corrected as shown below:

Column 39, line 27 change "wearing a derreal" to --wearing a dermal--

Column 39, line 30 change "into a dermat" to --into a dermal--

Column 40, line 47 change "A. Derreal Allergic" to --A. Dermal Allergic--

Column 42, line 34 change "antigert" to --antigen--

Column 43, line 13 change "10 mg per mi" to --10 mg per ml--

Column 50, line 34 change "Assisted Derreal" to --Assisted Dermal--

Signed and Sealed this

Seventh Day of May, 1996

Attest:

BRUCE LEHMAN

Attesting Officer

Commissioner of Patents and Trademarks